(12) United States Patent
Metcalfe et al.

(10) Patent No.: US 12,193,751 B2
(45) Date of Patent: Jan. 14, 2025

(54) PREOPERATIVE SURGICAL PLANNING SYSTEMS AND METHODS FOR GENERATING AND UTILIZING ANATOMICAL MAKEUP CLASSIFICATIONS

(71) Applicant: ARTHREX, INC., Naples, FL (US)

(72) Inventors: Nick Metcalfe, Bonita Springs, FL (US); Ryan Megger, Chagrin Falls, OH (US)

(73) Assignee: ARTHREX, INC., Naples, FL (US)

( * ) Notice: Subject to any disclaimer, the term of this patent is extended or adjusted under 35 U.S.C. 154(b) by 137 days.

(21) Appl. No.: 17/474,639

(22) Filed: Sep. 14, 2021

(65) Prior Publication Data

US 2023/0083517 A1    Mar. 16, 2023

(51) Int. Cl.
*A61B 34/10*      (2016.01)
*G16H 20/40*      (2018.01)

(52) U.S. Cl.
CPC ............. *A61B 34/10* (2016.02); *G16H 20/40* (2018.01); *A61B 2034/102* (2016.02); *A61B 2034/105* (2016.02)

(58) Field of Classification Search
CPC .............. A61B 34/10; A61B 2034/102; A61B 2034/105; G16H 20/40
See application file for complete search history.

(56) References Cited

U.S. PATENT DOCUMENTS

| | | |
|---|---|---|
| 8,532,807 B2 | 9/2013 | Metzger |
| 9,101,394 B2 | 8/2015 | Arata et al. |
| 9,129,054 B2 | 9/2015 | Nawana et al. |
| 9,271,848 B2 | 3/2016 | Brooks |
| 9,320,604 B2 | 4/2016 | Miles et al. |
| 9,665,686 B2 | 5/2017 | Van Vorhis et al. |
| 9,700,292 B2 | 7/2017 | Nawana et al. |

(Continued)

FOREIGN PATENT DOCUMENTS

| | | |
|---|---|---|
| JP | 5474303 B2 | 2/2014 |
| WO | 2018/067966 A8 | 4/2018 |

(Continued)

OTHER PUBLICATIONS

Saini, R., Kumar, P., Kaur, B., Roy, P. P., Dogra, D. P., & Santosh, K. C. (2019). Kinect sensor-based interaction monitoring system using the BLSTM neural network in healthcare. International Journal of Machine Learning and Cybernetics, 10, 2529-2540. (Year: 2019).*

(Continued)

*Primary Examiner* — Bijan Mapar
(74) *Attorney, Agent, or Firm* — Carlson, Gaskey & Olds, P.C.

(57) ABSTRACT

Improved surgical planning systems and methods are provided for planning orthopaedic procedures, including preoperatively, intra-operatively, and/or post-operatively to create, edit, execute, and/or review surgical plans. The surgical planning systems and methods may be utilized for planning and implementing orthopaedic procedures to restore functionality to a joint. In some embodiments, the systems and methods provide preoperative surgical planning based on anatomical makeup classifications that characterize anatomical differences within a representative patient population.

20 Claims, 15 Drawing Sheets

(56) References Cited

U.S. PATENT DOCUMENTS

| | | | |
|---|---|---|---|
| 9,717,508 B2 | 8/2017 | Iannotti et al. | |
| 9,730,628 B2 | 8/2017 | Iasemidis et al. | |
| 9,741,263 B2 | 8/2017 | Iannotti et al. | |
| 9,827,051 B2 | 11/2017 | Arata et al. | |
| 9,913,691 B2 | 3/2018 | Brooks | |
| 9,913,692 B2 | 3/2018 | Arata et al. | |
| 9,916,421 B2 | 3/2018 | Vorhis et al. | |
| 9,918,740 B2 | 3/2018 | Uthgenannt et al. | |
| 10,130,378 B2 | 11/2018 | Bryan | |
| 10,172,675 B2 | 1/2019 | Mahfouz | |
| 10,327,852 B2 | 6/2019 | Meridew et al. | |
| 10,449,003 B2 | 10/2019 | Reid et al. | |
| 10,452,238 B2 | 10/2019 | Nikou et al. | |
| 10,512,496 B2 | 12/2019 | Iannotti et al. | |
| 10,537,390 B2 | 1/2020 | Varadarajan et al. | |
| 10,595,943 B2 | 3/2020 | Barsoum et al. | |
| 10,624,655 B2 | 4/2020 | Iannotti et al. | |
| 10,660,705 B2 | 5/2020 | Piron et al. | |
| 10,660,709 B2 | 5/2020 | Chaoui | |
| 10,736,697 B2 | 8/2020 | Chaoui et al. | |
| 10,739,963 B2 | 8/2020 | Nikou et al. | |
| 10,973,580 B2 | 4/2021 | Berend et al. | |
| 11,083,525 B2 | 8/2021 | Varadarajan et al. | |
| 11,419,680 B2 | 8/2022 | Kontaxis et al. | |
| 11,443,846 B2 | 9/2022 | Schoenefeld et al. | |
| 11,464,569 B2 | 10/2022 | Ambers et al. | |
| 11,478,168 B2 | 10/2022 | Fleig et al. | |
| 11,488,721 B2 | 11/2022 | Otto et al. | |
| 11,532,402 B2 | 12/2022 | Farley et al. | |
| 2004/0102866 A1 | 5/2004 | Harris et al. | |
| 2004/0233387 A1 | 11/2004 | Huang et al. | |
| 2007/0219561 A1 | 9/2007 | Lavallee et al. | |
| 2012/0276509 A1 | 11/2012 | Iannotti et al. | |
| 2014/0013565 A1 | 1/2014 | MacDonald et al. | |
| 2014/0257402 A1 | 9/2014 | Barsoum | |
| 2014/0272881 A1 | 9/2014 | Barsoum | |
| 2014/0278322 A1 | 9/2014 | Jaramaz et al. | |
| 2014/0303990 A1 | 10/2014 | Schoenefeld et al. | |
| 2015/0093734 A1 | 4/2015 | Kaouk | |
| 2015/0261922 A1 | 9/2015 | Nawana et al. | |
| 2016/0210412 A1 | 7/2016 | Zellner et al. | |
| 2017/0143494 A1* | 5/2017 | Mahfouz | A61F 2/30942 |
| 2017/0296205 A1 | 10/2017 | Iannotti et al. | |
| 2018/0033338 A1 | 2/2018 | Iannotti et al. | |
| 2018/0233222 A1 | 8/2018 | Daley et al. | |
| 2018/0358120 A1 | 12/2018 | Schoenefeld et al. | |
| 2019/0005186 A1 | 1/2019 | Nikou et al. | |
| 2019/0231431 A1 | 8/2019 | Paszicsnyek | |
| 2019/0380792 A1 | 12/2019 | Poltaretskyi et al. | |
| 2019/0388153 A1 | 12/2019 | Running et al. | |
| 2020/0030034 A1 | 1/2020 | Kontaxis et al. | |
| 2020/0113632 A1 | 4/2020 | Varadarajan et al. | |
| 2020/0188026 A1 | 6/2020 | de Souza et al. | |
| 2020/0219626 A1 | 7/2020 | Otto et al. | |
| 2020/0243199 A1 | 7/2020 | Farley et al. | |
| 2020/0246075 A1 | 8/2020 | Dohmen et al. | |
| 2020/0246077 A1 | 8/2020 | Chaoui | |
| 2020/0275976 A1* | 9/2020 | McKinnon | A61B 90/37 |
| 2020/0395118 A1 | 12/2020 | Codd et al. | |
| 2021/0000380 A1 | 1/2021 | West et al. | |
| 2021/0015560 A1 | 1/2021 | Boddington et al. | |
| 2021/0093385 A1 | 4/2021 | Morvan et al. | |
| 2021/0093414 A1 | 4/2021 | Moore et al. | |
| 2021/0100620 A1 | 4/2021 | Chaoui et al. | |
| 2021/0104325 A1 | 4/2021 | Chaoui et al. | |
| 2021/0307833 A1 | 10/2021 | Farley et al. | |
| 2021/0315640 A1 | 10/2021 | Dees, Jr. et al. | |
| 2021/0322148 A1 | 10/2021 | Mitra et al. | |
| 2021/0346036 A1* | 11/2021 | Macdessi | A61F 2/461 |
| 2022/0039868 A1 | 2/2022 | Chaoui et al. | |
| 2022/0054197 A1 | 2/2022 | Plessers et al. | |
| 2022/0059212 A1 | 2/2022 | Chaoui et al. | |
| 2022/0059213 A1 | 2/2022 | Chaoui et al. | |
| 2022/0117663 A1 | 4/2022 | McGuan et al. | |
| 2022/0117755 A1 | 4/2022 | McGuan et al. | |
| 2022/0273281 A1 | 9/2022 | McKinnon et al. | |

FOREIGN PATENT DOCUMENTS

| | | |
|---|---|---|
| WO | 2018107042 A3 | 6/2018 |
| WO | 2019/245849 A1 | 12/2019 |
| WO | 2019/245854 A3 | 12/2019 |
| WO | 2019245865 A1 | 12/2019 |
| WO | 2020/037308 A1 | 2/2020 |
| WO | 2020033568 A2 | 2/2020 |
| WO | 2020056443 A1 | 3/2020 |
| WO | 2020072255 A1 | 4/2020 |
| WO | 2020/123706 A1 | 6/2020 |
| WO | 2020123702 A1 | 6/2020 |
| WO | 2020123709 A1 | 6/2020 |
| WO | 2020/163324 A1 | 8/2020 |
| WO | 2020/163352 A1 | 8/2020 |
| WO | 2020/163358 A1 | 8/2020 |
| WO | 2020163317 A1 | 8/2020 |
| WO | 2020163318 A1 | 8/2020 |
| WO | 2020227661 A1 | 11/2020 |
| WO | 2022066693 A1 | 3/2022 |
| WO | 2022076773 A1 | 4/2022 |

OTHER PUBLICATIONS

Simon P et al; "3D Image-Based Morphometric Analysis of the Scapular Neck Length in Subjects Undergoing Reverse Shoulder Arthroplasty," Clinical Anatomy, John Wiley & Sons, Hoboken, NJ, US, vol. 31, No. 1, Jul. 27, 2017, pp. 43-55, XP071744703, ISSN; 0897-3806, DOI: 10.1002/CA.22911.

Steinhaus Michael E et al: "Handheld Navigation Device and Patient-Specific Cutting Guides Result in Similar Coronal Alignment for Primary Total Knee Arthroplasty: a Retrospective Matched Cohort Study," HSS Jurnal, Springer US, Boston, vol. 12, No. 3, Feb. 29, 2016, pp. 224-234, XP036057677, ISSN: 1556-3316, DOI 10.1007/S11420-015-9484-2.

International Search Report and Written Opinion of the International Searching Authority for International Applicatoin No. PCT/US2022/043287 dated Feb. 6, 2023.

International Preliminary Report on Patentability for International application No. PCT/US2022/043287 dated Mar. 28, 2024.

* cited by examiner

PREOPERATIVE SURGICAL PLANNING SYSTEMS AND METHODS FOR GENERATING AND UTILIZING ANATOMICAL MAKEUP CLASSIFICATIONS

BACKGROUND

This disclosure is directed to surgical planning, and more particularly to improved surgical planning systems and methods for planning orthopedic procedures.

Arthroplasty is a type of orthopedic surgical procedure performed to repair or replace diseased joints. Surgeons may desire to establish a surgical plan for preparing a surgical site, selecting an implant, and placing the implant at the surgical site prior to performing arthroplasty in order to improve outcomes. Surgical planning may include capturing an image of the surgical site and determining a position of an implant based on the image.

SUMMARY

This disclosure relates to improved surgical planning systems and methods.

The surgical planning system and methods of this disclosure may be utilized in some implementations for planning orthopaedic procedures, including pre-operatively, intra-operatively, and/or post-operatively to create, edit, execute, and/or review surgical plans. The surgical planning systems and methods may be utilized for planning and implementing orthopaedic procedures to restore functionality to a joint.

A surgical planning system may include, inter alia, a processor configured to create a plurality of anatomical makeup classifications based on a plurality of predefined modes that characterize anatomical differences within a representative patient population and a plurality of standard deviations of anatomical variances contained within each of the plurality of predefined modes. A memory device of the system may be operably coupled to the processor and may be configured to store the plurality of anatomical makeup classifications.

A computer implemented surgical planning method may include, inter alia, identifying a plurality of predefined modes within a statistical shape model of a representative patient population, establishing a plurality of standard deviations of anatomical variances contained within each of the plurality of predefined modes, creating, via a processor of a surgical planning system that is configured to interface with the statistical shape model, a plurality of anatomical makeup classifications based on the plurality of predefined modes and the plurality of standard deviations of anatomical variances, and storing the plurality of anatomical makeup classifications within a memory device of the surgical planning system.

The embodiments, examples, and alternatives of the preceding paragraphs, the claims, or the following description and drawings, including any of their various aspects or respective individual features, may be taken independently or in any combination. Features described in connection with one embodiment are applicable to all embodiments, unless such features are incompatible.

The various features and advantages of this disclosure will become apparent to those skilled in the art from the following detailed description. The drawings that accompany the detailed description can be briefly described as follows.

DETAILED DESCRIPTION

This disclosure is directed to improved surgical planning systems and methods for planning orthopaedic procedures, including pre-operatively, intra-operatively, and/or post-operatively to create, edit, execute, and/or review surgical plans. The surgical planning systems and methods may be utilized for planning and implementing orthopaedic procedures to restore functionality to a joint. These and other features of this disclosure are discussed in greater detail in the following paragraphs of this detailed description.

Figure 1:
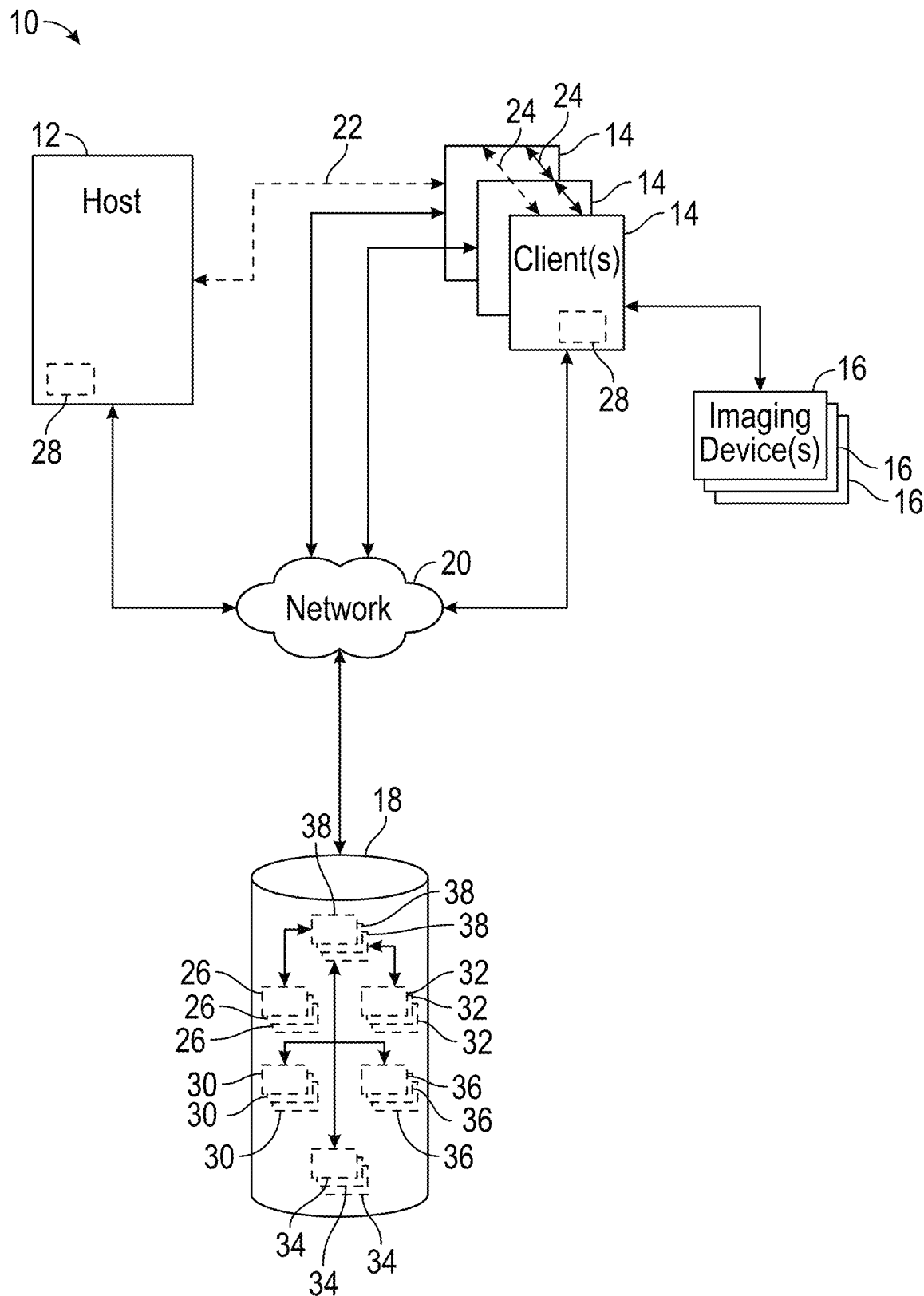
FIG. 1 schematically illustrates an exemplary surgical planning system.

FIG. 1 illustrates an exemplary surgical planning system 10 (hereinafter referred to as "the system 10"). The system 10 may be used for planning orthopaedic procedures, including pre-operatively, intra-operatively, and/or post-operatively to create, edit, review, refine, and/or execute surgical plans. The system 10 may be utilized for various orthopaedic and other surgical procedures, such as an arthroplasty to repair a joint, for example.

Shoulder arthroplasty may be periodically referenced throughout this disclosure to illustrate or emphasize certain features of the system 10. However, the teachings of this disclosure are not intended to be limited to any particular joint of the human musculoskeletal system and should therefore be understood as being applicable to the shoulder, knee, hip, ankle, wrist, etc. Moreover, the teachings of this disclosure are not intended to be limited to arthroplasty procedures and are therefore applicable to the repair of fractures and/or other deformities within the scope of this disclosure.

The system 10 may include, among other things, at least one host computer 12, one or more client computers 14, one or more imaging devices 16, a cloud-based storage system 18, and a network 20. The system 10 may include a greater or fewer number of subsystems within the scope of this disclosure.

The host computer 12 may be configured to execute one or more software programs. In some implementations, the host computer 12 may be more than one computer jointly configured to process software instructions serially or in parallel.

The host computer 12 may be in communication with the network 20, which itself may include one or more computing devices. The network 20 may be a private local area network (LAN), a private wide area network (WAN), the Internet, or a mesh network, for example.

The host computer 12 and each client computer 14 may include one or more of a computer processor, memory, storage means, network device and input and/or output devices and/or interfaces. The input devices may include a keyboard, mouse, etc. The output devices may include a monitor, speakers, printers, etc. The memory may, for example, include UVPROM, EEPROM, FLASH, RAM, ROM, DVD, CD, a hard drive, or other computer readable medium that may store data and/or other information relating to the surgical planning and implementation techniques disclosed herein. The host computer 12 and each client computer 14 may be a desktop computer, laptop computer, smart phone, tablet, virtual machine, or any other computing device. The interfaces may facilitate communication with the other systems and/or components of the network 20.

Each client computer 14 may be configured to communicate with the host computer 12 either directly, such as via a direct client interface 22, or over the network 20. In other implementations, the client computers 14 are configured to communicate with each other directly via a peer-to-peer interface 24.

Each client computer 14 may be coupled to one or more of the imaging devices 16. Each imaging device 16 may be configured to capture or acquire one or more images 26 of patient anatomy residing within a scan field (e.g., window) of the imaging device 16. The imaging device 16 may be configured to capture or acquire two dimensional (2D) and/or three dimensional (3D) greyscale and/or color images 26. Various imaging devices 16 may be utilized, including but not limited to an X-ray machine, a computerized tomography (CT) machine, or a magnetic resonance imaging (MRI) machine, for obtaining one or more images 26 of a patient.

The client computers 14 may also be configured to execute one or more software programs, such as those associated with various surgical planning tools. Each client computer 14 may be operable to access and locally and/or remotely execute a planning environment 28 for creating, editing, executing, refining, and/or reviewing one or more surgical plans 36 during pre-operative, intra-operative and/or post-operative phases of a surgery. The planning environment 28 may be a standalone software package or may be incorporated into another surgical tool. The planning environment 28 may be configured to communicate with the host computer 12 either over the network 20 or directly through the direct client interface 22.

The planning environment 28 may be further configured to interact with one or more of the imaging devices 16 to capture or acquire images 26 of patient anatomy. The planning environment 28 may provide a display or visualization of one or more images 26, bone models 30, implant models 32, transfer models 34, and/or surgical plans 36 via one or more graphical user interfaces (GUI). Each image 26, bone model 30, implant model 32, transfer model 34, surgical plan 36, and other data and/or information may be stored in one or more files or records according to a specified data structure.

The planning environment 28 may include various modules for performing the desired planning functions. For example, as further discussed below, the planning environment 28 may include a data module for accessing, retrieving, and/or storing data concerning the surgical plans 36, a display module for displaying the data (e.g., within one or more GUIs), a spatial module for modifying the data displayed by the display module, and a comparison module for determining one or more relationships between selected bone models and selected implant models. However, a greater or fewer number of modules may be utilized, and/or one or more of the modules may be combined to provide the disclosed functionality.

The storage system 18 may be operable to store or otherwise provide data from/to other computing devices, such as the host computer 12 and/or the one or more client computers 14, of the system 10. The storage system 18 may be a storage area network device (SAN) configured to communicate with the host computer 12 and/or the client computers 14 over the network 20, for example. Although shown as a separate device of the system 10, the storage system 18 may in some implementations be incorporated within or directly coupled to the host computer 12 and/or client computers 14. The storage system 18 may be configured to store one or more of computer software instructions, data, database files, configuration information, etc.

In some implementations, the system 10 may be a client-server architecture configured to execute computer software on the host computer 12, which may be accessible by the client computers 14 using either a thin client application or a web browser that can be executed on the client computers 14. The host computer 12 may load the computer software instructions from local storage, or from the storage system 18, into memory and may execute the computer software using the one or more computer processors.

The system 10 may further include one or more databases 38. The databases 38 may be stored at a central location, such as on the storage system 18. In another implementation, one or more databases 38 may be stored at the host computer 12 and/or may be a distributed database provided by one or more of the client computers 14. Each database 38 may be a relational database configured to associate one or more images 26, bone models 30, implant models 32, and/or transfer models 34 to each other and/or to a respective surgical plan 36. Each surgical plan 36 may be associated with the anatomy of a respective patient. Each image 26, bone model 30, implant model 32, transfer model 34, and surgical plan 36 may be assigned a unique identifier or database entry for storage on the storage system 18. Each database 38 may be configured to store data and other information corresponding to the images 26, bone models 30, implant models 32, transfer models 34, and surgical plans 36 in one or more database records or entries, and/or may be configured to link or otherwise associate one or more files corresponding to each respective image 26, bone model 30, implant model 32, transfer model 34, and surgical plan 36. The various data stored in the database(s) 38 may correspond to respective patient anatomies from prior surgical cases, and may be arranged into one or more predefined categories such as sex, age, ethnicity, defect category, procedure type, anatomical makeup classification, surgeon, facility or organization, etc.

Each image 26 and bone model 30 may include data and other information obtained from one or more medical devices or tools, such as the imaging devices 16. The bone models 30 may include one or more digital images and/or coordinate information relating to an anatomy of the patient obtained or derived from image(s) 26 captured or otherwise obtained by the imaging device(s) 16.

Each implant model 32 and transfer model 34 may include coordinate information associated with a predefined design or a design established or modified by the planning environment 28. The predefined design may correspond to one or more components. The planning environment 28 may incorporate and/or interface with one or more modeling packages, such as a computer aided design (CAD) package, to render the models 30, 32, and 34 as two-dimensional (2D) and/or three-dimensional (3D) volumes or constructs, which may overlay one or more of the images 26 in a display screen of a GUI.

The implant models 32 may correspond to implants and components of various shapes and sizes. Each implant may include one or more components that may be situated at a surgical site including screws, anchors, grafts, etc. Each implant model 32 may correspond to a single component or may include two or more components that may be configured to establish an assembly. Each implant and associated component(s) may be formed of various materials, including metallic and/or non-metallic materials. Each bone model 30, implant model 32, and transfer model 34 may correspond to 2D and/or 3D geometry, and may be utilized to generate a wireframe, mesh, and/or solid construct in a GUI.

Each surgical plan 36 may be associated with one or more of the images 26, bone models 30, implant models 32, and/or transfer models 34. The surgical plan 36 may include various parameters associated with the images 26, bone models 30, implant models 32, and/or transfer models 34. For example, the surgical plan 36 may include parameters relating to bone density and bone quality associated with patient anatomy captured in the image(s) 26. The surgical plan 36 may include parameters including spatial information relating to relative positioning and coordinate information of the selected bone model(s) 30, implant model(s) 32, and/or transfer model(s) 34.

The surgical plan 36 may define one or more revisions to a bone model 30 and information relating to a position of an implant model 32 and/or transfer model 34 relative to the original and/or revised bone model 30. The surgical plan 36 may include coordinate information relating to the revised bone model 30 and a relative position of the implant model 32 and/or transfer model 34 in one or more predefined data structure(s). The planning environment 28 may be configured to implement one or more revisions to the various models, either automatically or in response to user interaction with the user interface(s). Revisions to each bone model 30, implant model 32, transfer model 34, and/or surgical plan 36 may be stored in one or more of the databases 38, either automatically and/or in response to user interaction with the system 10.

One or more surgeons and/or other staff users may be presented with the planning environment 28 via the client computers 14 and may simultaneously access each image 26, bone model 30, implant model 32, transfer model 34, and surgical plan 36 stored in the database(s) 38. Each user may interact with the planning environment 28 to create, view, refine, and/or modify various aspects of the surgical plan 36. Each client computer 14 may be configured to store local instances of the images 26, bone models 30, implant models 32, transfer models 34, and/or surgical plans 36, which may be synchronized in real-time or periodically with the database(s) 38. The planning environment 28 may be a stand-alone software package executed on a client computer 14 or may be provided as one or more web-based services executed on the host computer 12, for example.

The system 10 described above may be configured for preoperatively planning surgical procedures. The preoperative planning provided by the system 10 may include, but is not limited to, features such as constructing a virtual model of a patient's anatomy, classifying the virtual model, identifying landmarks within the virtual model, selecting and orienting virtual implants within the virtual model, etc.

Figure 2:
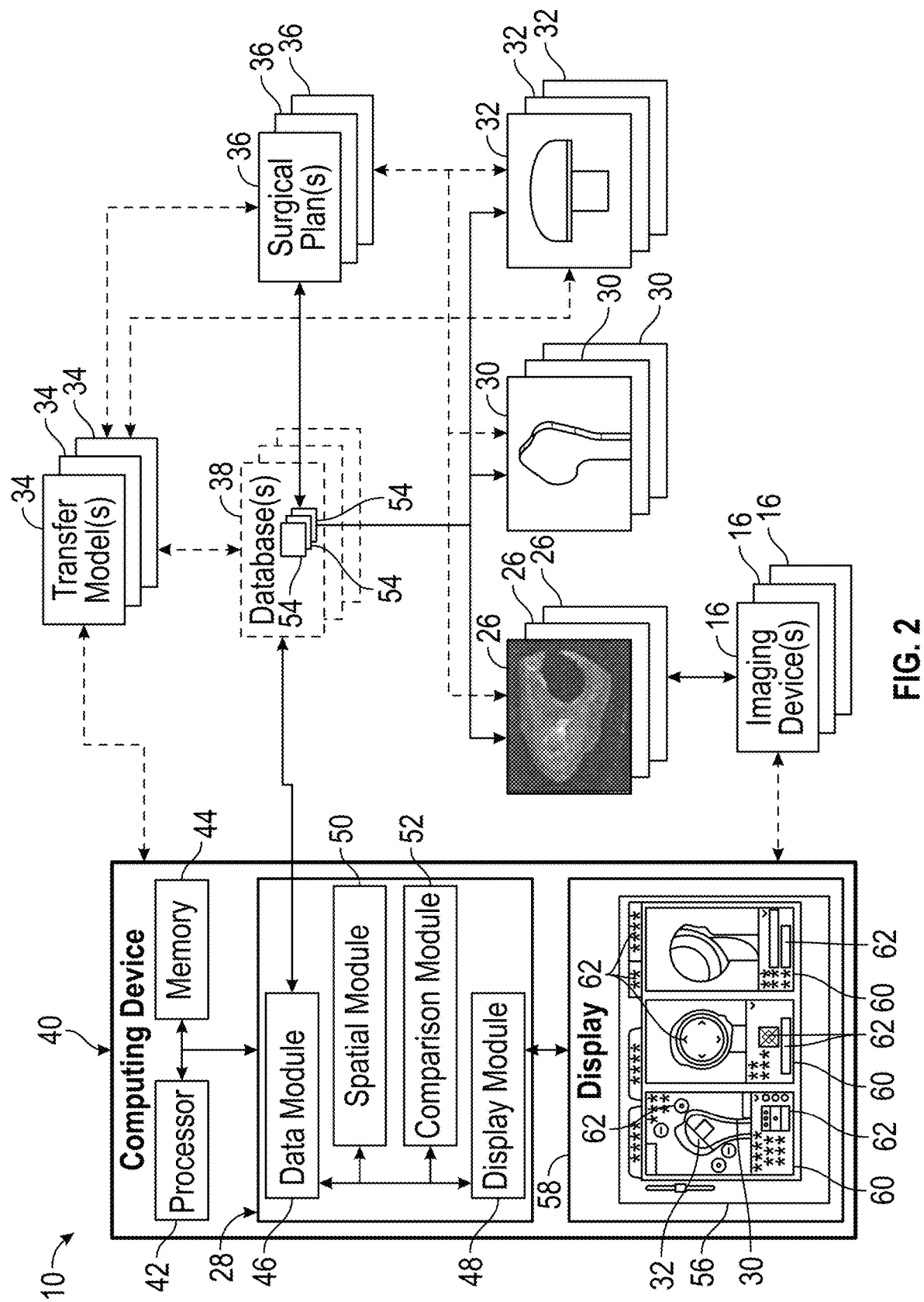
FIG. 2 schematically illustrates exemplary aspects of the surgical planning system of FIG. 1.

Referring now to FIG. 2, with continuing reference to FIG. 1, the system 10 may include a computing device 40 including at least one processor 42 coupled to a memory 44 capable of storing computer executable instructions. The computing device 40 may be considered representative of any of the computing devices disclosed herein, including but not limited to the host computer 12 and/or the client computers 14. The processor 42 may be configured to execute one or more of the planning environments 28 for creating, editing, executing, refining, and/or reviewing one or more surgical plans 36 and any associated bone models 30, implant models 32, and transfer models 34 during pre-operative, intra-operative, and/or post-operative phases of a surgery.

The processor 42 can be a custom made or commercially available processor, central processing unit (CPU), or generally any device for executing software instructions. The memory 44 can include any one or combination of volatile memory elements and/or nonvolatile memory elements. The processor 42 may be operably coupled to the memory 44 and may be configured to execute one or more programs stored in the memory 44 based on various inputs received from other devices or data sources.

The planning environment 28 may include at least a data module 46, a display module 48, a spatial module 50, and a comparison module 52. Although four modules are shown, it should be understood that a greater or fewer number of modules could be utilized, and/or further that one or more of the modules could be combined to provide the disclosed functionality.

The data module 46 may be configured to access, retrieve, and/or store data and other information in the database(s) 38 corresponding to one or more images 26 of patient anatomy, bone model(s) 30, implant model(s) 32, transfer model(s) 34, and/or surgical plan(s) 36. The data and other information may be stored in one or more databases 38 as one or more records or entries 54. In some implementations, the data and other information may be stored in one or more files that are accessible by referencing one or more objects or memory locations referenced by the entries 54.

The memory 44 may be configured to access, load, edit, and/or store instances of one or more images 26, bone models 30, implant models 32, transfer models 34, and/or surgical plans 36 in response to one or more commands from the data module 46. The data module 46 may be configured to cause the memory 44 to store a local instance of the image(s) 26, bone model(s) 30, implant model(s) 32, transfer model(s) 34, and/or surgical plan(s) 36, which may be synchronized with the entries 54 stored in the database(s) 38.

The data module 46 may be configured to receive data and other information corresponding to at least one or more images 26 of patient anatomy from various sources, such as the imaging device(s) 16, for example. The data module 46 may be further configured to command the imaging device 16 to capture or acquire the images 26 automatically or in response to user interaction.

The display module 48 may be configured to display data and other information relating to one or more surgical plans 36 in at least one graphical user interface (GUI) 56, including one or more of the images 26, bone models 30, implant models 32, and/or transfer models 34. The computing device 40 may incorporate or be coupled to a display device 58. The display module 48 may be configured to allow the display device 58 to display information in the user interface 56. A surgeon or other user may interact with the user interface 56 within the planning environment 28 to view one or more images 26 of patient anatomy and/or any associated bone models 30, implant models 32, and transfer models 34. The surgeon or other user may interact with the user interface 56 via the planning environment 28 to create, edit, execute, refine, and/or review one or more surgical plans 36.

The user interface 56 may include one or more display windows 60 and one or more objects 62 that may be presented within the display windows 60. The display windows 60 may include any number of windows, and the objects 62 may include any number of objects within the scope of this disclosure.

A surgeon or user may interact with the user interface 56, including the objects 62 and/or display windows 60, to retrieve, view, edit, store, etc., various aspects of a respective surgical plan 36, which may include information from the selected image(s) 26, bone model(s) 30, implant model(s) 32 and/or transfer model(s) 34. The objects 62 may include graphics such as menus, tabs, buttons, drop-down lists, directional indicators, etc. The objects 62 may be organized in one or more menu items associated with the respective display windows 60. Geometric objects, including selected image(s) 26, bone model(s) 30, implant model(s) 32, transfer model(s) 34, and/or other information relating to the surgical plan 36, may be displayed in one or more of the display windows 60. Each transfer model 34 may include one or more surgical instruments used to implant a selected implant as part of the surgical plan 36.

[moss] The surgeon may interact with the objects 62 to specify various aspects of the surgical plan 36. For example, the surgeon may select one of the tabs to view or specify aspects of the surgical plan 36 for one portion of a joint, such as a glenoid, for example, and may select another one of the tabs to view or specify aspects of the surgical plan 36 for another portion of the joint, such as a humerus, for example. The surgeon make further take various measurements (e.g., linear, angular, tissue density, etc.) of the joint as part specifying aspects of the surgical plan 36.

The surgeon may interact with the menu items to select and specify various aspects of the bone models 30, implant models 32, and/or transfer models 34 from the database 38. For example, the display module 48 may be configured to display one or more bone models 30 together with the respective image(s) 26 of the patient anatomy and implant models 32 selected in response to user interaction with the user interface 56. The user may interact with the drop-down lists of the objects 62 within the display windows 60 to specify implant type, resection angle, and implant size. The resection angle menu item may be further associated with a resection plane.

The user may also interact with various buttons to change (e.g., increase or decrease) a resection angle. The user may interact with buttons adjacent the selected implant model 32 to change (e.g., increase or decrease) a size of a component of the selected implant model 32. The buttons may be overlaid onto or may be situated adjacent to the display windows 60.

The user may further interact with directional indicators to move a portion of the selected implant model 32 in different directions (e.g., up, down, left, right) in one of the display windows 60. The surgeon may drag or otherwise move the selected implant model 32 to a desired position in the display window 60 utilizing a mouse or other input device, for example. The surgeon may interact with one of the drop-down lists to specify a type and/or size of a component of the selected implant model 32.

The display module 48 may be configured to superimpose one or more of the bone models 30, the implant models 32, and the transfer models 34 over one or more of the images 26 within one or more of the display windows 60. The implant model 32 may include one or more components that establish an assembly. At least a portion of the implant model 32 may be configured to be at least partially received in a volume of a selected one of the bone models 30. In some implementations, the implant model 32 may have an articulation surface dimensioned to mate with an articular surface of an opposed bone or implant.

The display windows 60 may be configured to display the images 26, bone models 30, implant models 32, and/or transfer models 34 at various orientations. The display module 48 may be configured to display two dimensional (2D) representation(s) of the selected bone model(s) 30, implant model(s) 32, and/or transfer model(s) 34 in the some of the display windows 60, and may be configured to display 3D representation(s) of the selected bone model 30, implant model 32, and/or transfer model(s) 34 in another of the display windows 60, for example. The surgeon may interact with the user interface 56 to move (e.g., up, down, left, right, rotate, etc.) the selected bone model 30, selected implant model 32, and/or selected transfer model 34 in 2D space and/or 3D space. Other implementations for displaying 2D and/or 3D representations in the various display windows 60 are further contemplated within the scope of this disclosure.

The display module 48 may be further configured such that the selected image(s) 26, bone model(s) 30, implant model(s) 32, and/or transfer model(s) 34 may be selectively displayed and hidden (e.g., toggled) in one or more of the display windows 60 in response to user interaction with the user interface 56, which may provide the surgeon with enhanced flexibility in reviewing aspects of the surgical plan 36. For example, the surgeon may interact with drop-down lists of the objects 62 to selectively display and hide components of the selected implant model 32 in one of the display windows 60.

The selected bone model 30 may correspond to a bone associated with a joint, including any of the exemplary joints disclosed herein. The display module 48 may be configured to display a sectional view of the selected bone model 30 and selected implant model 32 in one or more of the display windows 60, for example. The sectional view of the bone model(s) 30 may be presented or displayed together with the associated image(s) 26 of the patient anatomy.

The spatial module 50 may be configured to establish one or more resection planes along the selected bone model 30. A volume of the selected implant model 32 may be at least partially received in a volume of the selected bone model 30 along the resection plane(s). The resection plane(s) may be defined by a resection angle.

The spatial module 50 may be further configured to cause the display module 48 to display an excised portion of the selected bone model 30 to be displayed in one of the display windows 60 in a different manner than a remainder of the bone model 30 on an opposed side of the resection plane. For example, the excised portion of the bone model 30 may be hidden from display in the display window 60 such that the respective portion of the 26 of the patient anatomy is shown. In other implementations, the excised portion of the selected bone model 30 may be displayed in a relatively darker shade. The spatial module 50 may determine the excised portion by comparing coordinates of the bone model 30 with respect to a position of the resection plane, for example. The user may interact with one or more buttons of the objects 62 to toggle between a volume of previous and revised (e.g., resected) states of the selected bone model 30.

The planning environment 28 may be further configured such that changes in one of the display windows 60 are synchronized with each of the other windows 60. The changes may be synchronized between the display windows 60 automatically and/or manually in response to user interaction.

The surgeon may utilize various instrumentation and devices to implement each surgical plan 36, including preparing the surgical site and securing one or more implants to bone or other tissue to restore functionality to the respective joint. Each of the transfer models 34 may be associated with a respective surgical instrument or device (e.g., transfer guides, etc.) or a respective implant model 32.

The surgical plan 36 may be associated with one or more positioning objects such as a guide pin (e.g., guide wire or Kirschner wire) dimensioned to be secured in tissue to position and orient the various instrumentation, devices and/or implants. The display module 48 may be configured to display a virtual position and virtual axis in one or more of the display windows 60. The virtual position may be associated with a specified position of the positioning object relative to the patient anatomy (as represented by the image(s) 26). The virtual axis may extend through the virtual position and may be associated with a specified orientation of the positioning object relative to the patient anatomy. The spatial module 50 may be configured to set the virtual position and/or virtual axis in response to placement of a respective implant model 32 relative to the bone model 30 and associated patient anatomy. The virtual position and/or virtual axis may be set and/or adjusted automatically based on a position and orientation of the selected implant model 32 relative to the selected bone model 30 and/or in response to user interaction with the user interface 56.

The spatial module 50 may be further configured to determine one or more collision or contact points associated with the patient anatomy. The contact points may be associated with one or more landmarks or other surface features along the bone model 30 and/or other portions of the patient anatomy. Each contact point may be established along an articular surface or non-articular surface of a joint. The spatial module 50 may be configured to set the contact points based on the virtual position, virtual axis, and/or position and orientation of the respective implant model 32 relative to the patient anatomy. The spatial module 50 may be configured to cause the display module 48 to display the contact points in one or more of the display windows 60. In some implementations, the contact points may be set and/or adjusted automatically based on a position of the implant model 32 and/or in response to user interaction with the user interface 56. The virtual position, virtual axis, and/or contact points may be stored in one or more entries 54 in the database 38 and may be associated with the respective surgical plan 36.

The comparison module 52 may be configured to generate or set one or more parameters associated with implementing the surgical plan 36. The parameters may include one or more settings or dimensions associated with the respective transfer models 34. The parameters may be based on the virtual position, virtual axis, and/or contact points. The comparison module 52 may be configured to determine one or more settings or dimensions associated with the respective transfer models 34 relative to the patient anatomy, bone model(s) 30, implant model(s) 32, virtual position, virtual axis, and/or contact points CP. The dimensions and settings may be utilized to form a physical instance of each respective transfer model 34. The settings may be utilized to specify a position and orientation of each respective transfer model 34 relative to the implant model 32 and/or bone model 30. The settings may be utilized to configure one or more transfer members (e.g., objects) and related instrumentation or devices associated with the transfer model 34. The comparison module 52 may be configured to generate the settings and/or dimensions such that the transfer model 34 contacts one or more predetermined positions at or along the bone model 30 or patient anatomy in an installed position when coupled to the respective implant model 32. The predetermined positions may include one or more of the contact points. The settings and dimensions may be communicated utilizing various techniques, including one or more graphics in the user interface 56 or output files. The settings and/or dimensions may be stored in one or more entries 54 in the database 38 associated with the transfer models 34.

The user may interact with a list of the objects 62 associated with one of the display windows 60 to select a desired transfer model 34 from the database 38. The display module 48 may be configured to display the selected transfer model 34 in the display windows 60 at various positions and orientations. The spatial module 50 may be configured to set an initial position of the selected transfer model 34 according to the virtual position, virtual axis, and/or contact points.

The user may interact with the user interface 56 to set or adjust a position and/or orientation of the selected transfer model 34. The user may interact with directional indicators of the objects 62 to move the selected transfer model 34 and/or virtual position in different directions (e.g., up, down, left, right) in the display windows 60. The surgeon may drag or otherwise move the selected transfer model 34 and/or virtual position to a desired position in the display windows 60 utilizing a mouse or other input device, for example. The user may interact with rotational indicators of the objects to adjust a position and/or orientation of the transfer model 34 about the virtual axis relative to the selected bone model 30 and/or implant model 32. The user may interact with tilt indicators of the objects 62 to adjust an orientation of the selected transfer model 34 and associated virtual axis at the virtual position relative to the selected bone model 30 and/or implant model 32. The user may interact with other buttons and/or directional indicators to cause the transfer model 34 to articulate or otherwise move. The transfer model 34 may be articulated or otherwise moved independently or synchronously, which may occur manually in response to user interaction and/or automatically in response to situating the transfer model 34 relative to the bone model 30 and/or implant model 32. Movement of the transfer model 34 may cause an automatic adjustment to the respective contact points.

Various transfer members may be utilized with the planning environment 28 to implement the surgical plan(s) 36. Each transfer member may be associated with a respective transfer model 34. The transfer members may be incorporated into transfer guides, implants, and/or assemblies to set a position and orientation of the respective implant prior to fixing or otherwise securing the implant at a surgical site.

Figure 3:
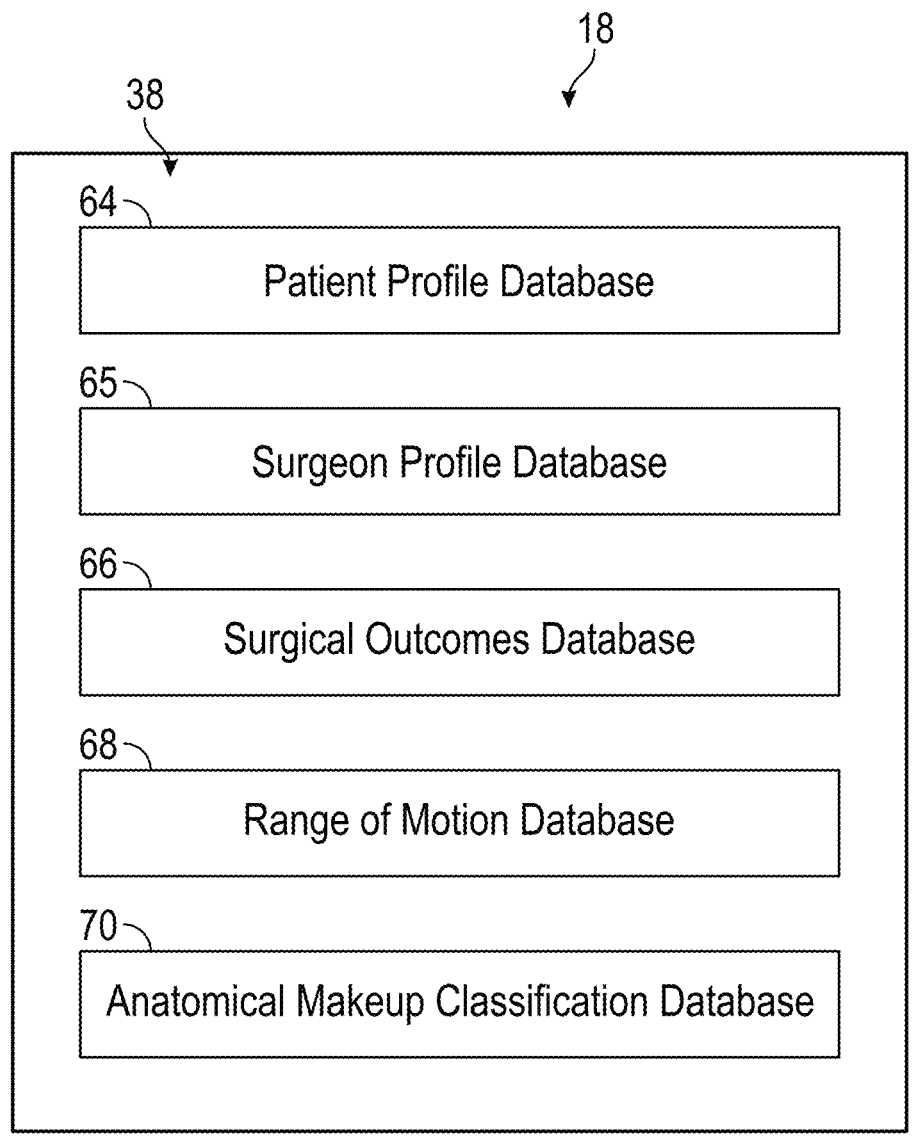
FIG. 3 schematically illustrates exemplary cloud-based databases that can be accessed by a surgical planning system.

Referring now to FIG. 3, with continued reference to FIG. 2, the computing device 40 may interface with the storage system 18 over the network 20 for accessing various databases 38 stored thereon in order to establish and implement the surgical plans 36.

The databases 38 of the storage system 18 may include a patient profile database 64, a surgeon profile database 65, a surgical outcomes database 66, a range of motion database 68, and an anatomical makeup classification database 70. Additional databases could be stored on and accessed from the storage system 18 within the scope of this disclosure. Moreover, although shown as separate databases, one or more of the databases could be combined or linked together. For example, the anatomical makeup classification database 70 could be combined or linked with the surgical outcomes database 66, the range of motion database 68, or both.

The patient profile database 64 may include information that is part of an indexed and stored record or entry related to one or more current patients associated with the system 10. The information stored on the patient profile database 64 may include the sex, age, ethnicity, height, weight, defect category, procedure type, surgeon, facility or organization, dominant joint, acts of daily living/lifestyle goals profile (e.g., desired post-surgery range of motion for abduction, adduction, external rotation, internal rotation, extension, flexion, external rotation combined with 60° abduction, internal rotation with 60° abduction, etc.), current surgical plan information, etc. for each patient. The patient profile database 64 may further store or link to the images 26 for a given patient.

The surgeon profile database 65 may include information that is part of indexed and stored records or entries related to one or more surgeon users associated with the system 10. The information stored on the surgeon profile database 65 may include the surgeon's name, facility or organization, historical data concerning the types of prior surgeries planned by the surgeon using the system 10, data concerning the types of implants included in the surgeon's preoperative surgical plans, data concerning the actual implants utilized in the surgeon's prior surgeries, etc. In some implementations, the surgeon profile database 65 may interface with the patient profile database 64 for linking each surgeon from the surgeon profile database 65 to his/her patients listed in the patient profile database 64.

The surgical outcomes database 66 may include information that is part of indexed and stored records or entries related to one or more prior patients associated with the system 10. The surgical outcomes database 66 may be created based on information logged by surgeons and/or other staff users after performing each surgery and at each follow-up visit for indicating the progress of the prior patient. The information stored on the surgical outcomes database 66 may include the sex, age, ethnicity, height, weight, defect category, procedure type, specific implants used, surgeon, facility or organization, dominant joint, visual analog pain scores, ASES scores, achieved acts of daily living/lifestyle profile (e.g., achieved post-surgery range of motion for abduction, adduction, external rotation, internal rotation, extension, flexion, external rotation combined with 60° abduction, internal rotation with 60° abduction, etc.), surgical plan information, etc. for each prior patient. The surgical outcomes database 66 may additionally store or link to preoperative and postoperative images 26 for each prior patient.

The range of motion database 68 may include information that is part of indexed and stored records or entries related to one or more current and prior patients associated with the system 10. The range of motion database 68 may store range of motion data derived from range of motion simulations performed by the computing device 40 for each surgical plan 36. The range of motion data may include information related to simulated joint motions (e.g., abduction/adduction, flexion/extension, internal/external rotation, etc.), identified contact or collision points for various implant positions, angular arc and mode of collision (e.g., implant-to-implant, implant-to-bone, bone-to-bone, etc.) for various implant positions, adjusted center of rotation of implants in multiple increments and offset directions for various implant positions, etc.

The anatomical makeup classification database 70 may store a plurality of anatomical makeup classifications that characterize anatomical differences and variances within the anatomical differences within a representative patient population for one or more intended surgeries (e.g., total shoulder, reverse shoulder, etc.). In some implementations, the representative patient population may be derived by analyzing image data, such as images from the prior patients stored on the surgical outcomes database 66 and/or any other imaging source, associated with a plurality of prior patients who have already received the intended surgery. Each of the plurality of anatomical makeup classifications is a numerical classification of an anatomical makeup of a bone or a joint of the representative patient population.

Figure 4:
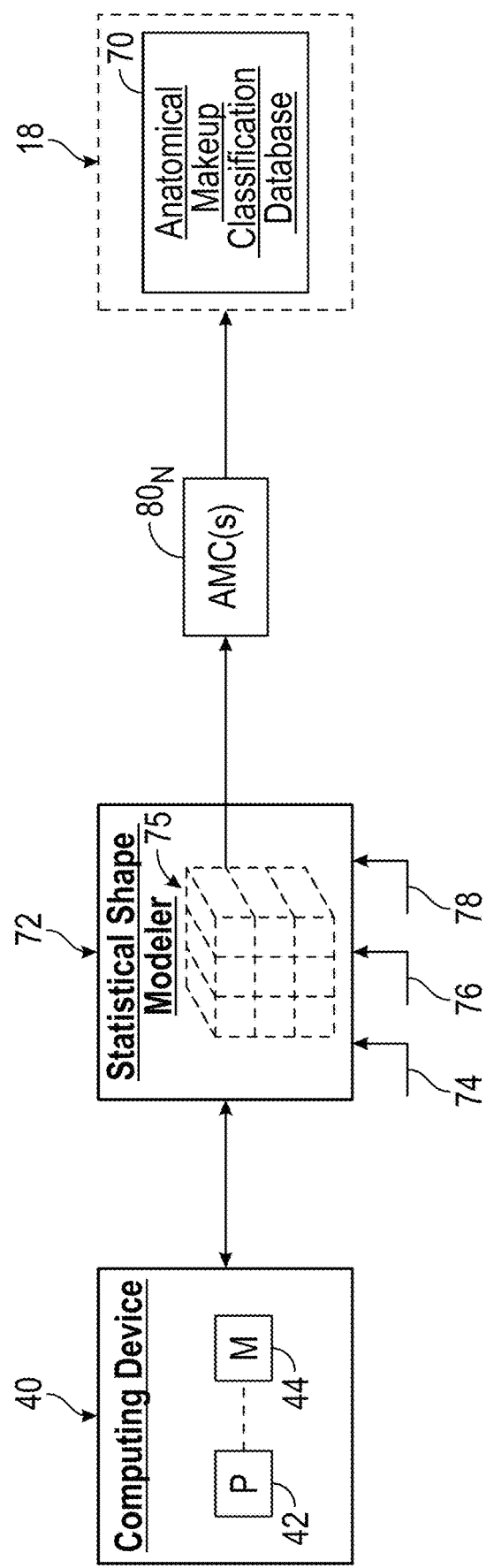
FIG. 4 schematically illustrates additional exemplary aspects of the surgical planning system of FIG. 1.

Referring now to FIG. 4, with continued reference to FIGS. 1-3, the computing device 40 may interface with a statistical shape modeler 72 for creating the anatomical makeup classification database 70. The statistical shape modeler 72 may be a software package stored in the memory 44 of the computing device 40 or in the storage system 18 and which may be executed by the processor 42.

The statistical shape modeler 72 may receive a plurality of sets of image data 74 associated with a bone or joint of interest. In some implementations, the sets of image data 74 is made up of tens of thousands of sets of image data. Each set of image data 74 may include 2D and/or 3D anatomical images specific to prior patients of a representative patient population for the bone or joint of interest and related to a given type of surgery. The statistical shape modeler 72 may analyze the plurality of sets of image data 74 for constructing a statistical shape model 75.

As an input, the statistical shape modeler 72 may receive a plurality of predefined modes 76 to be used for analyzing the plurality of sets of image data 74. Each of the modes 76 is a descriptor configured for characterizing anatomical differences in the bone or joint associated with the statistical shape model 75. Exemplary modes 76 that may be provided to the statistical shape modeler 72 may include but are not limited to size of glenoid, size of scapula, amount of inclination, amount of version, projected amount of glenoid and sagittal neck length, angle of glenoid relative to scapular neck, critical shoulder angle, projection of acromion and/or coracoid, size of humeral head, varus/valgus of humeral head, varus/valgus of femur and/or tibia, internal/external rotation of femur and/or tibia, integrity of subscapularis, deltoid, and/or supraspinatus, ML and AP width, intercondylar notch depth, tibial slope, Q-angle of the knee, ACL/PCL stability, MCL/LCL stability, amount of flexion, amount of extension, quality and amount of soft tissue surrounding joint, patellar tracking angle, bone density, bone quality subluxation percentage, anatomical landmarks, joint space, pre-operative range of motion, any combinations of the foregoing, etc.

In some implementations, at least seven different modes may be utilized by the statistical shape modeler 72 to characterize the statistical shape model 75. However, a greater or fewer number of modes may be provided within the scope of this disclosure.

In some implementations, the modes 76 may not be predefined. Rather, the statistical shape modeler 72 may be programmed to utilize artificial intelligence (e.g. a neural network) or machine learning to extrapolate the modes that best relate to the bone or joint being modeled within the statistical shape model 75.

As another input, the statistical shape modeler 72 may receive a plurality of predefined standard deviations 78 to be used for analyzing the plurality of sets of image data 74. Each standard deviation 78 may represent anatomical variances (e.g., distances between features, orientation of features, relative features, etc.) contained within each of the plurality of predefined modes 76. The standard deviations 78 may be used to validate a percentile coverage of the representative patient population that is represented within the statistical shape model 75. In some implementations, at least seven different standards of deviation (e.g., −3, −2, −1, 0, 1, 2, and 3) may be utilized by the statistical shape modeler 72 to further characterize all anatomical variances contained within the anatomies described within the statistical shape model 75. However, a greater or fewer number of standard deviations could be utilized within the scope of this disclosure.

The statistical shape modeler 72 may, in response to commands from the processor 42, combine the plurality of standard deviations 78 with the plurality of predefined modes 76 to assign a plurality of anatomical makeup classifications $80_N$, wherein N is any number, to the bone or joint associated with the statistical shape model 75 in order to categorize the anatomical makeup of the entire patient population represented within the statistical shape model 75. Each anatomical makeup classification $80_N$ may then be saved in the anatomical makeup classification database 70 of the storage system 18.

Figure 5:
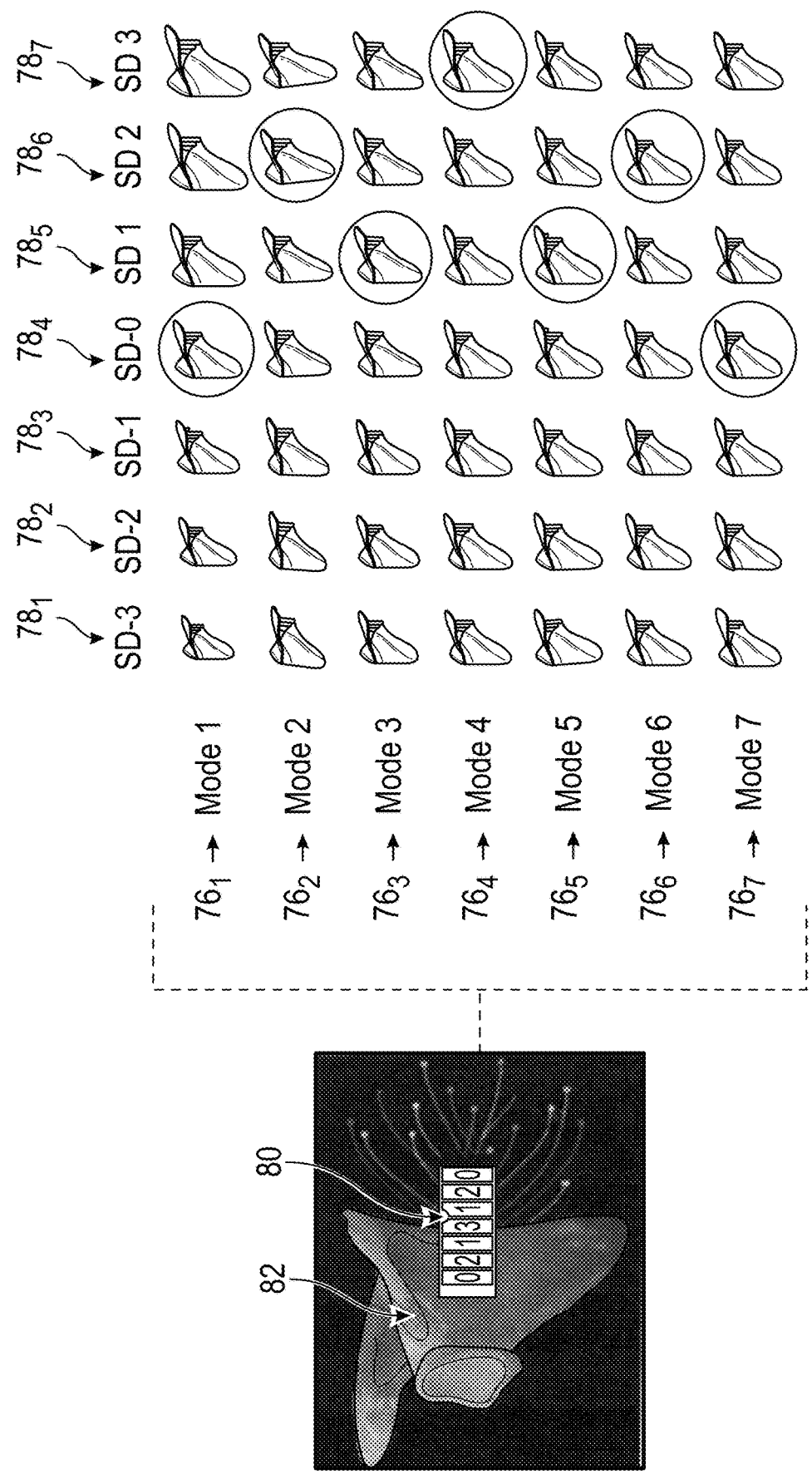
FIG. 5 schematically illustrates an exemplary anatomical makeup classification that can be assigned by a surgical planning system.

FIG. 5 illustrates an exemplary anatomic makeup classification 80 as assigned to a specific bone model 82 derived from the statistical shape model 75. In an embodiment, the bone model 82 is a 3D model of a scapula of a shoulder joint. However, other bones and joints could also be classified in a similar manner.

The statistical shape modeler 72 of FIG. 4 may analyze the bone model 82 in respect to each of a plurality of modes $76_1$ to $76_7$, in order to characterize any anatomical differences in the bone model 82 compared to the other similar bones/joints associated with the statistical shape model 75. Of course, a greater or fewer number of modes are possible.

The statistical shape modeler 72 may further characterize any anatomical variances contained within each of the plurality of predefined modes $76_1$-$76_7$ by analyzing each of the modes with respect to a plurality of standard deviations $78_1$-$78_7$. Of course, a greater or fewer number of standards of deviation are possible.

In the implementation shown in FIG. 5, the bone model 82 is assigned the numerical value 0213120 as its anatomical makeup classification 80. This numerical value represents a standard of deviation of 0 within the first mode $76_1$, a standard of deviation of 2 within the second mode $76_2$, a standard of deviation of 1 within the third mode $76_3$, a standard of deviation of 3 within the fourth mode $76_4$, a standard of deviation of 1 in the fifth mode $76_5$, a standard of deviation of 2 within the sixth mode $76_6$, and a standard of deviation of 0 in the seventh mode $76_7$. The anatomical makeup classification 80 is a unique numeric identifier for describing the anatomy associated with the bone model 82.

Figure 6:
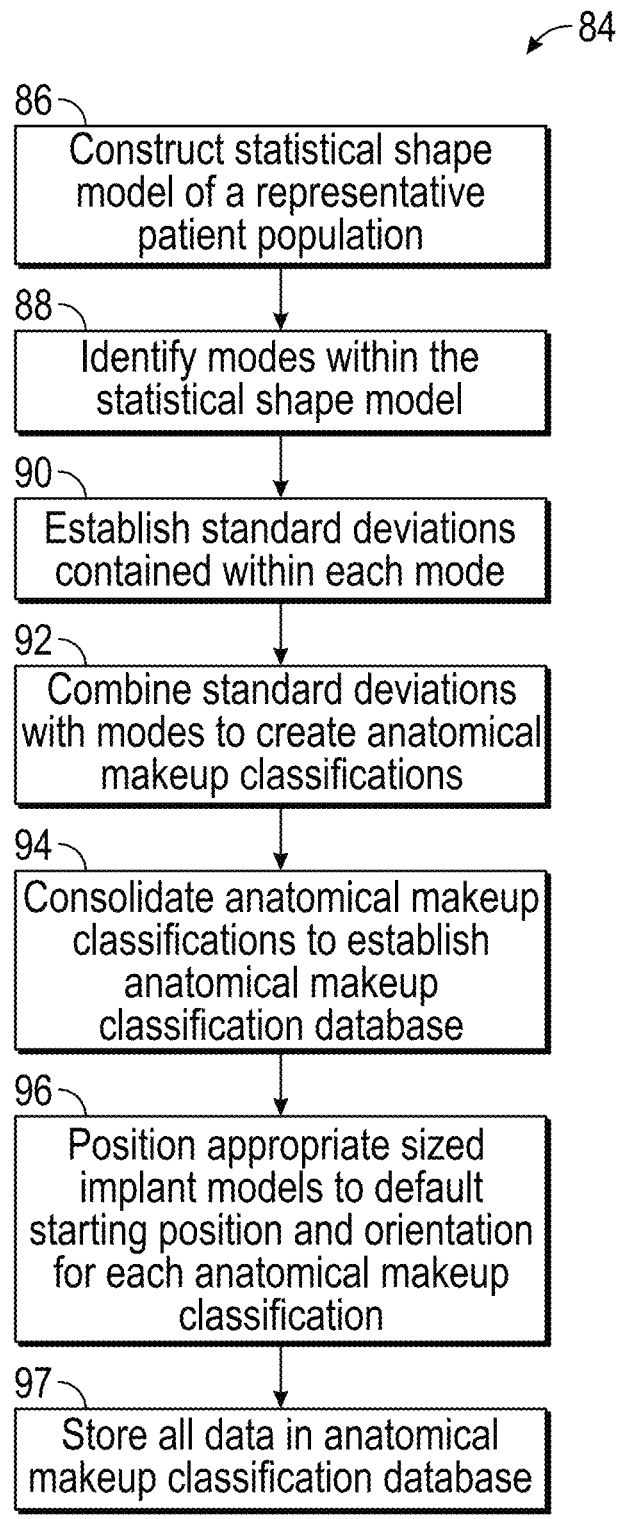
FIG. 6 schematically illustrates a method for establishing an anatomical makeup classification database of a surgical planning system.

FIG. 6, with continued reference to FIGS. 1-5, schematically illustrates a method 84 for creating the anatomical makeup classification database 70 described above. The method 84 may be performed as part of a surgical planning procedure. Fewer or additional steps than are recited below could be performed within the scope of this disclosure, and the recited order of steps is not intended to limit this disclosure. The system 10, via any of its associated computing devices and modules, may be configured to execute each of the steps of the method 84. In an exemplary implementation, the computing device 40 of the host computer 12 may be programmed to execute the method 84. However, other implementations are further contemplated within the scope of this disclosure.

A statistical shape model 75 that is representative of a patient population having pathologic anatomies associated with an intended surgery may be constructed at step 86. A plurality of modes 76 may be identified within the statistical shape model 75 at step 88. The modes 76 may characterize anatomical differences within the statistical shape model 75.

Next, at step 90, a plurality of standard deviations 78 of anatomical variances contained within each of the modes 76 may be established. The standard deviations 78 may be used to validate a percentile coverage of the representative patient population associated with the statistical shape model 75.

The standard deviations 78 may be combined with the modes 76 to create a plurality of unique anatomical makeup classifications 80 at step 92. At step 94, the anatomical makeup classifications 80 may be consolidated to form the anatomical makeup classification database 70. The anatomical makeup classification database 70 may therefore represent major variances within the representative patient population which may influence implant function.

As further part of the method 84, an appropriate sized implant model 32 may be selected and positioned to a default starting position and orientation relative to the bone or joint associated with each of the plurality of anatomical makeup classifications 80 at step 96. The default starting positions and orientations of the implant models 32 may therefore also be linked to and stored, at step 97, with the anatomical makeup classifications 80 as part of the anatomical makeup classification database 70.

Once built, the anatomical makeup classification database 70 may enable additional features, processes, and/or capabilities to be implemented within or executed by the system 10 for enhancing surgical planning Example implementations of such features are detailed below.

Figure 7:
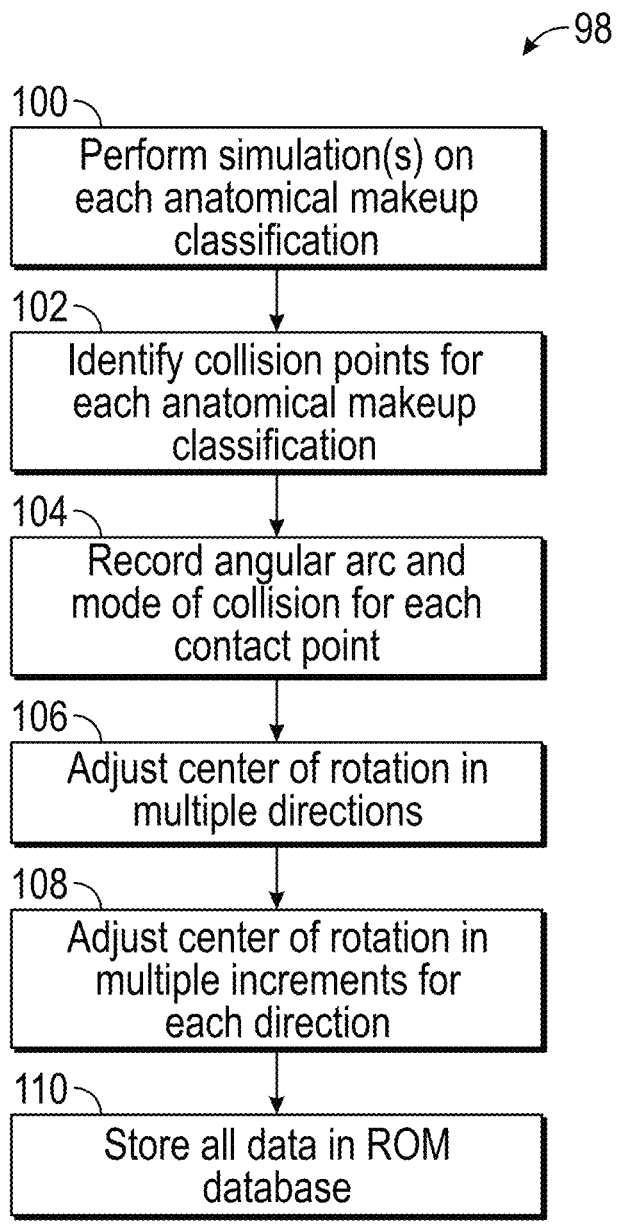
FIG. 7 schematically illustrates a method for establishing a range of motion database of a surgical planning system.

FIG. 7, for example, illustrates a method 98 for augmenting the range of motion database 68 with the information contained within the anatomical makeup classification database 70. The method 98 may be performed as part of a surgical planning procedure. Fewer or additional steps than are recited below could be performed within the scope of this disclosure, and the recited order of steps is not intended to limit this disclosure. The system 10, via any of its associated computing devices and modules, may be configured to execute each of the steps of the method 98. In an exemplary implementation, the computing device 40 of the host computer 12 may be programmed to execute the method 98. However, other implementations are further contemplated within the scope of this disclosure.

Figure 8:
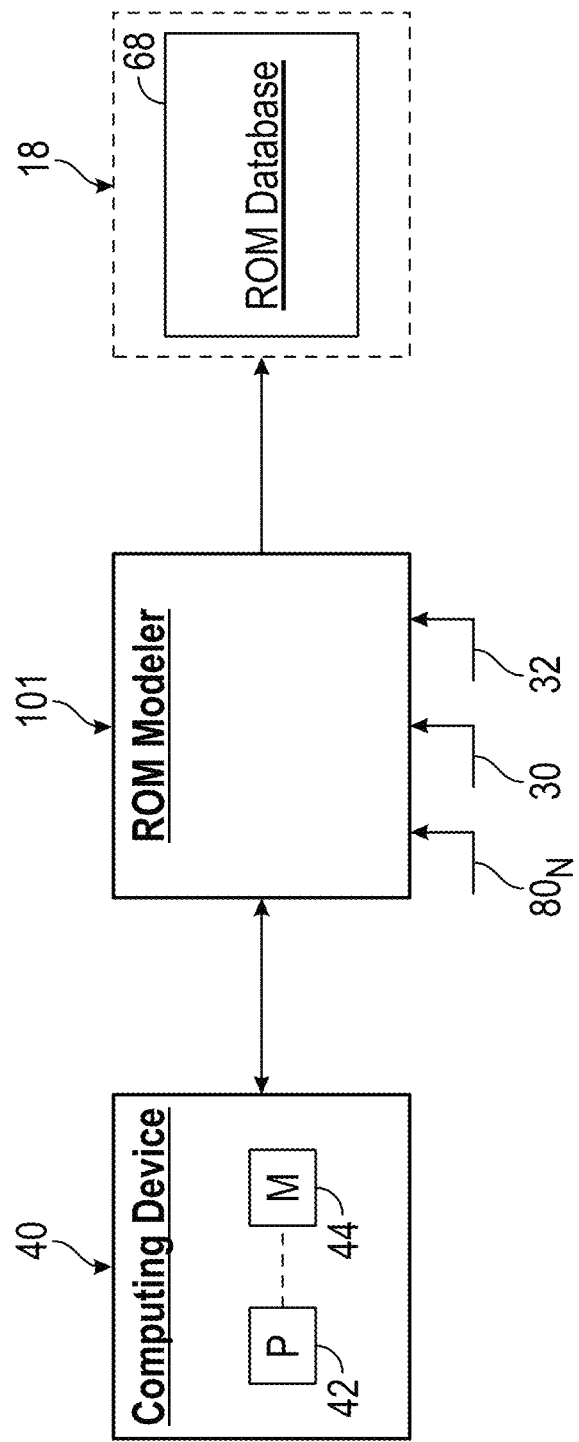
FIG. 8 schematically illustrates additional exemplary aspects of the surgical planning system of FIG. 1.

First, at step 100, one or more motion simulations may be performed on each anatomical makeup classification 80 stored on the anatomical makeup classification database 70. The motion simulations may be performed within a range of motion modeler 101, which may be a software package stored in the memory 44 of the computing device 40 or in the storage system 18 and which may be executed by the processor 42 (see, e.g., FIG. 8). The range of motion modeler 101 may receive each of the anatomical makeup classifications 80 (and each associated bone model 30 and implant model 32, including default implant starting positions and orientations) as inputs from the anatomical makeup classification database 70 when performing the motion simulations.

The range of motion simulations actually performed at step 100 will depend on the type of bone or joint being analyzed, among other criteria. Examples of the types of motions that can be simulated as part of step 100 of the method 98 include but are not limited to abduction/adduction, flexion/extension, internal/external rotation, etc.

Contact or collision points may be identified at step 102 for identifying the range of motion end points for each range of motion simulation performed on each anatomical makeup classification 80. The angular arc and mode of collision (e.g., implant-to-implant, implant-to-bone, bone-to-bone, etc.) for each contact point may be recorded at step 104.

The center of rotation of the implant models 32 positioned within the bone models 30 for each anatomical makeup classification 80 may be adjusted at step 106. In some implementations, this step may include adjusting each implant model 32 in at least three offset directions (e.g., medial, interior, and posterior) relative to the respective bone model 30 to simulation different positions of the implant models 32.

At step 108, the center of rotation of the implant model 32 for each anatomical makeup classification 80 may be adjusted relative to the respective bone model 30 in multiple increments for recording the angular arcs and collision modes associated with the adjusted positions. All range of motion data derived from the simulations performed at steps 100-108 may then be saved within the range of motion database 68 at step 110.

Figure 9:
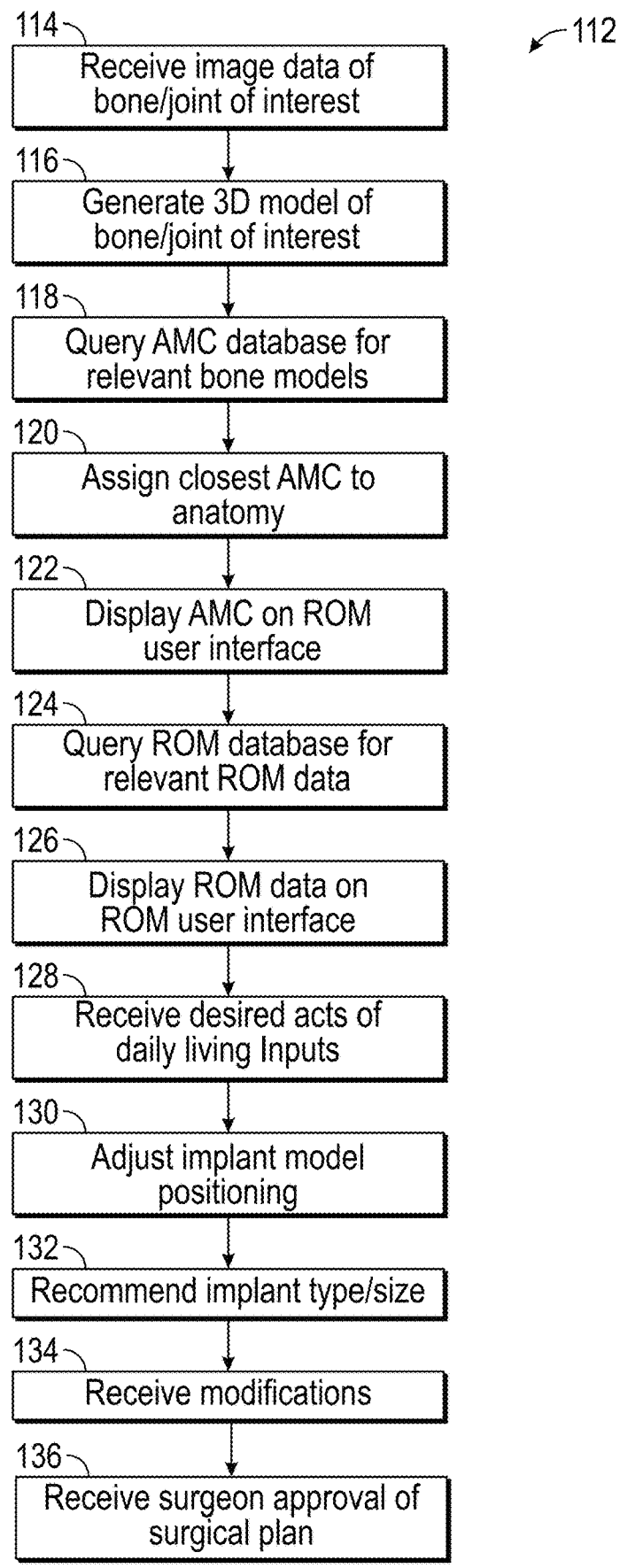
FIG. 9 schematically illustrates a method for planning an orthopedic procedure on a respective patient using a surgical planning system.

FIG. 9 schematically illustrates a method 112 for planning an orthopedic procedure for a respective patient using the system 10. The method 112 may be performed as part of a surgical planning procedure for preparing a surgical plan for the patient. Fewer or additional steps than are recited below could be performed within the scope of this disclosure, and the recited order of steps is not intended to limit this disclosure. The system 10, via any of its associated computing devices and modules, may be configured to execute each of the steps of the method 112. In an exemplary implementation, the computing device 40 of one or more of the client computers 14 may be programmed to execute the method 112. However, other implementations are further contemplated within the scope of this disclosure.

Image data of a bone or joint of interest of the patient may be received at step 114. The image data may be received directly from the imaging device 16 or may be acquired by accessing the record or entry associated with the patient from the patient profile database 64.

[moms] A 3D model of the bone or joint of interest may be generated at step 116. The planning environment 28 of the computing device 40 may incorporate and/or interface with one or more modeling packages, such as a computer aided design (CAD) package, to render the 3D model of the bone or joint of interest.

Next, at step 118, the computing device 40 may query the anatomical makeup classification database 70 to locate bone models stored therein that have similar anatomical makeup classifications. The anatomical makeup classification that is closest to the anatomy encompassed by the 3D model may then be assigned to the 3D model at step 120 and displayed on a range of motion user interface of the computing device 40 at step 122. As part of displaying the anatomical makeup classification, a confidence level indicator may be displayed within the range of motion user interface for visually indicating the similarity between the assigned anatomical makeup classification and the anatomy being analyzed. The confidence level indicator may be displayed as a percentage or any other visual indicator.

The range of motion database 68 may be queried at step 124 to obtain range of motion data that is relevant to the assigned anatomical makeup classification. The range of motion data associated with the assigned anatomical makeup classification, including information such as the angular arc and the mode of impingement, may be displayed on the range of motion user interface at step 126.

At step 128, the surgeon or other staff user of the system 10 may be queried to select the desired acts of daily living goals of the patient. The positioning of the implant model may be automatically adjusted relative to the bone model based on the selected acts of daily living at step 130. The system 10 may then output a recommended implant size/type and position and orientation for meeting the selected acts of daily living at step 132.

The surgeon may be prompted to modify the recommended implant type, positioning, and/or orientation per his/her clinical judgement at step 134. The method 112 may end at step 136 in response to receiving the surgeon's approval of the surgical plan. As part of this step, a comparison of the simulated range of motion results stored in the ROM database 68 to the range of motion achieved by the surgeon's planned positions and orientations may be presented to the user within a graphical user interface. This step may further include notifying the surgeon within the graphical user interface of any potential impact the proposed changes may have based on past surgical outcome data associated with prior patients having similar anatomical makeup classifications.

Figure 10:
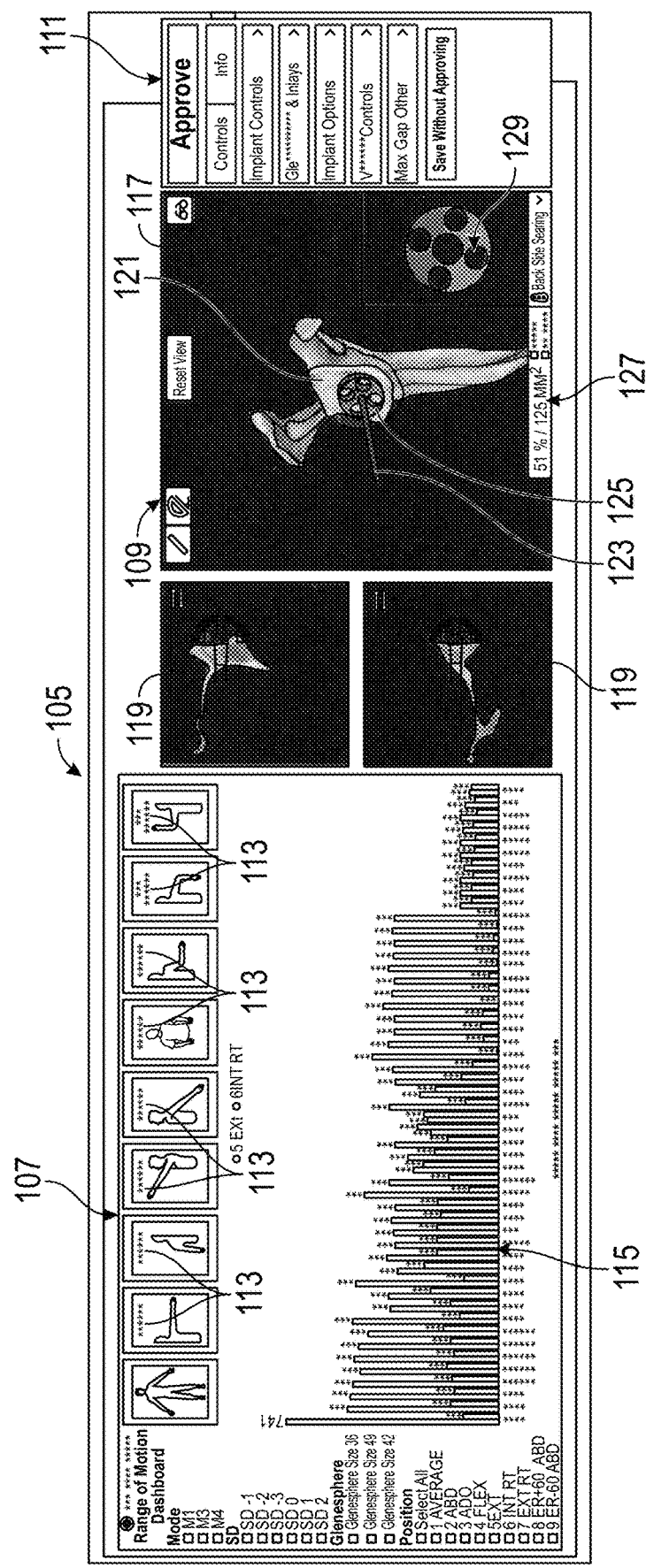
FIG. 10 illustrates an exemplary user interface of a surgical planning system.

FIG. 10 illustrates an exemplary range of motion user interface 105 that may be provided during the method 112 discussed above. The range of motion user interface 105 may be presented within the planning environment 28, for example.

The range of motion user interface 105 may include a range of motion dashboard 107, a display window 109, and a control panel 111. The range of motion dashboard 107 may present various range of motion data to the user. The range of motion dashboard 107 may include a plurality of selectable buttons 113 related to foundational joint motion expectations for the patient. The foundational joint motion expectations that may be represented by the buttons 113 may include but is not limited to desired post-surgery range of motion for abduction, adduction, external rotation, internal rotation, extension, flexion, external rotation combined with 60° abduction, and internal rotation combined with 60° abduction.

The range of motion dashboard 107 may further include a bar graph 115 for illustrating range of motion data for each of the foundational joint motion expectations. For example, the bar graph 115 may provide a visual display of the range of motion achieved for a selected foundational joint motion expectation for one or more AMCs that are closest to the anatomy of the patient that the surgical plan is being created for.

The display window 109 may include a 3D window 117 and multiple 2D windows 119. A virtual bone model 121 of the patient's anatomy may be displayed within the 3D window 117 and the 2D windows 119. A positioning of both a virtual guide pin 123 and a virtual implant 125 that is necessary for achieving the desired joint motion expectations may be displayed relative to the virtual bone model 121 to provide the user with information on how to best approach the surgery being planned.

The display window 109 may be manipulated using the control panel 111. For example, the control panel 111 may include a plurality of toggles, buttons, sliders, etc. that allow the user to modify various settings, such as the positioning of the virtual guide pin 123 and/or the virtual implant 125 relative to the virtual bone model 121. In an embodiment, a backside seating amount 127 and a color-coded backside seating map 129 may be provided on the display window 109 and may automatically update as adjustments are made to the virtual positions of the virtual guide pin 123 and the virtual implant 125 relative to the virtual bone model 121. The information presented in the display window 109 may also automatically update as the user pages through each of the buttons 113.

Figure 11:
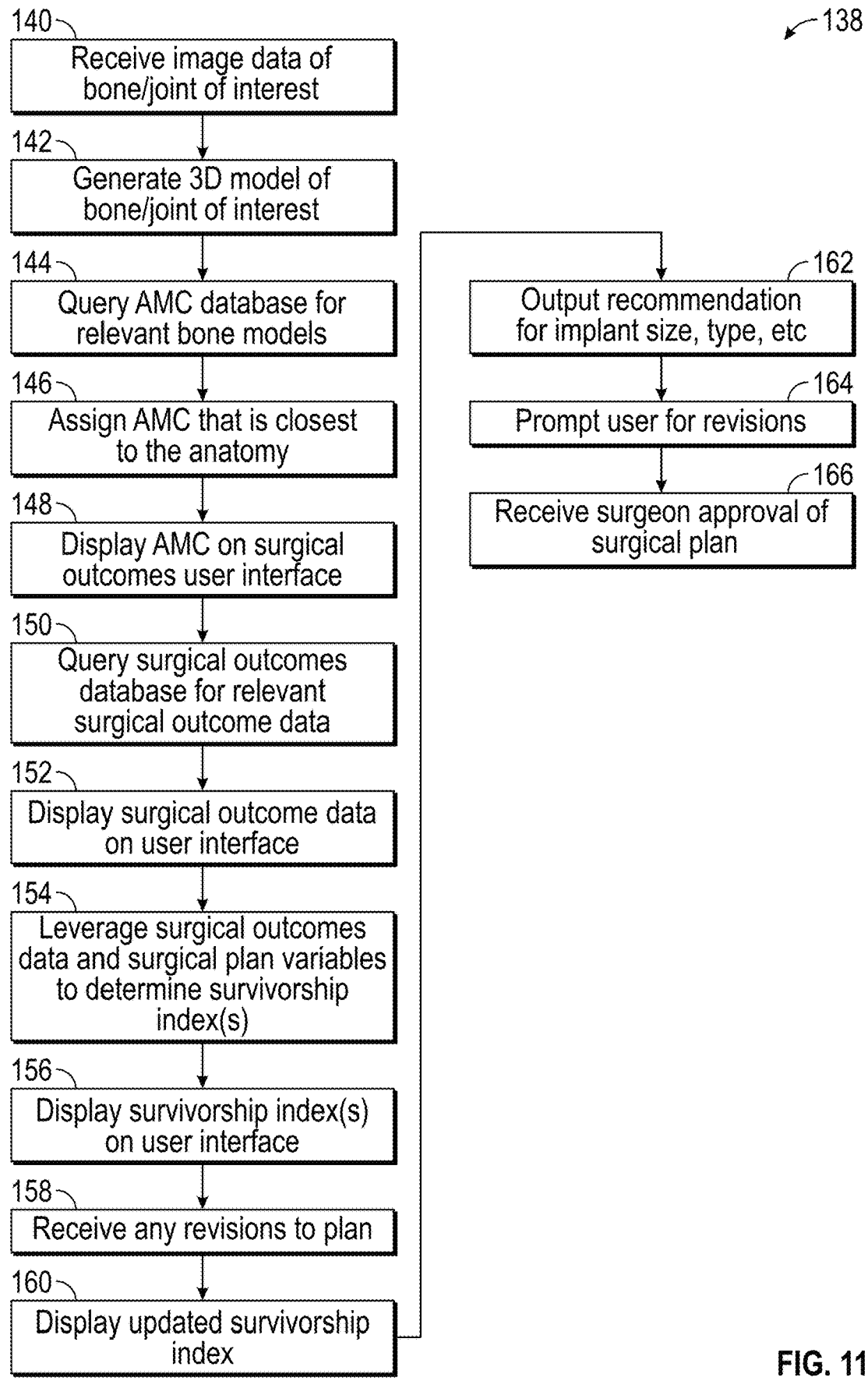
FIG. 11 schematically illustrates another exemplary method for planning an orthopedic procedure on a respective patient using a surgical planning system.

FIG. 11 schematically illustrates another method 138 for planning an orthopedic procedure for a respective patient using the system 10. The method 138 may be performed as part of a surgical planning procedure for preparing a surgical plan for the patient. Fewer or additional steps than are recited below could be performed within the scope of this disclosure, and the recited order of steps is not intended to limit this disclosure. The system 10, via any of its associated computing devices and modules, may be configured to execute each of the steps of the method 138. In an exemplary implementation, the computing device 40 of one or more of the client computers 14 may be programmed to execute the method 138. However, other implementations are further contemplated within the scope of this disclosure.

Image data of a bone or joint of interest of the patient may be received at step 140. The image data may be received directly from the imaging device 16 or may be acquired by accessing the record or entry associated with the patient from the patient profile database 64.

A 3D model of the bone or joint of interest may be generated at step 142. The planning environment 28 of the computing device 40 may incorporate and/or interface with one or more modeling packages, such as a computer aided design (CAD) package, to render the 3D model of the bone or joint of interest.

Next, at step 144, the computing device 40 may query the anatomical makeup classification database 70 to locate bone models stored therein that have anatomical makeup classifications that are similar to the anatomical makeup classification of the bone or joint of the patient. The anatomical makeup classification that is closest to the anatomy encompassed by the 3D model may then be assigned to the 3D model at step 146 and displayed on a surgical outcomes user interface of the computing device 40 at step 148. As part of displaying the anatomical makeup classification, a confidence level indicator may be displayed within the graphical user interface for visually indicating the similarity between the assigned anatomical makeup classification and the anatomy being analyzed. The confidence level indicator may be displayed as a percentage or any other visual indicator.

The surgical outcomes database 66 may be queried at step 150 to obtain surgical outcomes data that is most relevant to the assigned anatomical makeup classification. The surgical outcomes data associated with the assigned anatomical makeup classification may be displayed on the surgical outcomes user interface at step 152. The surgical outcomes data that is displayed to the user may be automatically updated in response to a user prompt, such as when the user changes the planned procedure type, for example.

In an embodiment, the surgical outcomes database 66 may be queried to locate prior surgeries that involved patients having an average bone density that is comparable to an estimated average bone density of a bone associated with the anatomy of the patient. This comparison can be used to recommend a particular surgical implant that is not incompatible with the average bone density of the bone under study, for example.

Next, at step 154, data from the surgical outcomes database 66 for the comparable anatomical makeup classifications and a plurality of variables associated with a surgical plan for operating on the patient may be leveraged in order to determine one or more survivorship predictive indexes. The variables may include factors such as surgical implant type, surgical implant size, surgical implant orientation, a surgical procedure type, a surgical implant backside seating configuration, a fastener orientation, or any combinations thereof. The variables are inputs to the system 10 that may be selected by the surgeon or staff user within the surgical outcomes user interface.

[mom] The determined survivorship predictive index may be displayed on the surgical outcomes user interface at step 156. Each survivorship predictive index may be a percentile representation of a confidence level that the surgical plan will result in a successful surgical outcome for at least a predefined amount of time. For example, based on the data of the comparable anatomical makeup classifications and the relevant variables selected/set by the surgeon, the system 10 may determine and display a survivorship predictive index of 40% at three years post-surgery for comparable patients who underwent a standard total shoulder arthroplasty procedure and a survivorship predictive index of 85% at three years post-surgery for comparable patients who underwent a reverse shoulder arthroplasty procedure, thus indicating to the surgeon that a more successful outcome for the patient could likely be obtained by performing a reverse shoulder arthroplasty procedure rather than a standard total shoulder arthroplasty procedure.

After displaying the survivorship predictive index displayed at step 156, the system 10 may prompt the surgeon for making any revisions to the variables associated with the current surgical plan at step 158. If revisions are received as inputs into the system 10, an updated survivorship predictive index may be displayed at step 160.

The system 10 may output a recommended procedure type, implant size/type, and implant position/orientation for best matching the comparable anatomical makeup classifications at step 162. The surgeon may be prompted to modify the recommended implant type, positioning, and/or orientation per his/her clinical judgement at step 164. The method 138 may end after receiving, at step 166, the surgeon's approval of the surgical plan.

Figure 12:
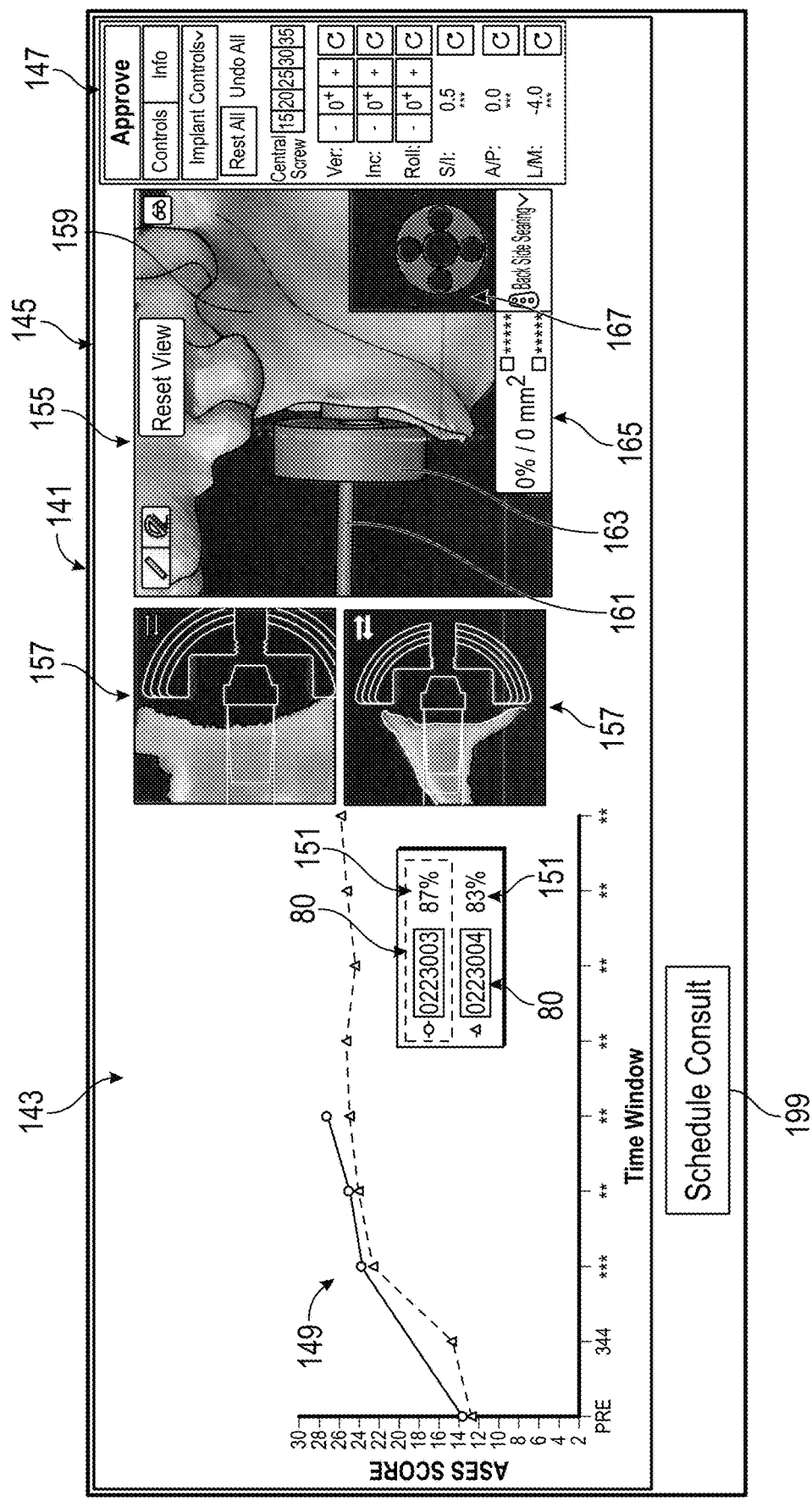
FIG. 12 illustrates another exemplary user interface of a surgical planning system.

FIG. 12 illustrates an exemplary surgical outcomes user interface 141 that may be provided during the method 138 discussed above. The surgical outcomes user interface 141 may be presented within the planning environment 28, for example.

The surgical outcomes user interface 141 may include a graphical listing 143 for displaying the anatomical makeup classifications 80 most similar to the anatomical makeup classification of the bone or joint of the patient, a display window 145, and a control panel 147.

The graphical listing 143 may include a graph 149 of ASES score versus time for each of the comparable anatomical makeup classifications 80 that are listed. Although two anatomical makeup classifications 80 are shown being listed in FIG. 12, the graphical listing 143 could provide a greater or fewer number of anatomical makeup classifications 80 within the scope of this disclosure.

The graphical listing 143 may further include a confidence level indicator 151 that may be displayed adjacent to each comparable anatomical makeup classification 80. The confidence level indicator 151 may be a percentage or any other visual indicator for visually indicating the similarity between the assigned anatomical makeup classification and the anatomy being analyzed. The user may select the desired comparable anatomical makeup classification 80 using an input selector 153, for example.

The display window 145 may include a 3D window 155 and multiple 2D windows 157. A virtual bone model 159 of the patient's anatomy may be displayed within the 3D window 155 and the 2D windows 157. A virtual guide pin 161 and a virtual implant 163 associated with the selected comparable anatomical makeup classification 80 may be displayed relative to the virtual bone model 159 to provide the user with information on how prior surgeries were conducted for patient's having the comparable anatomical makeup classification 80.

The display window 145 may be manipulated using the control panel 147. For example, the control panel 147 may include a plurality of toggles, buttons, sliders, etc. that allow the user to modify various settings, such as the positioning of the virtual guide pin 161 and/or the virtual implant 163 relative to the virtual bone model 159. In an embodiment, a backside seating amount 165 and a color-coded backside seating map 167 may be displayed on the display window 145 and may automatically update as adjustments are made to the virtual positions of the virtual guide pin 161 and the virtual implant 163 relative to the virtual bone model 159.

The surgical outcomes user interface 141 may further include a consult scheduling button 199. The user may press or otherwise actuate the consult scheduling button 199 in order to arrange a consultation with a surgeon who performed the prior surgery for the comparable anatomical makeup classification 80. Once the consult scheduling button 199 has been actuated, the user and the relevant surgeon may be presented with a series of prompts for coordinating and carrying out the consultation. The consultation may be conducted via chat room, telephone, video conference, etc. If desired, the identities of one or both of the requesting surgeon and the consulting surgeon may be kept confidential during the consultation.

Figure 13A:
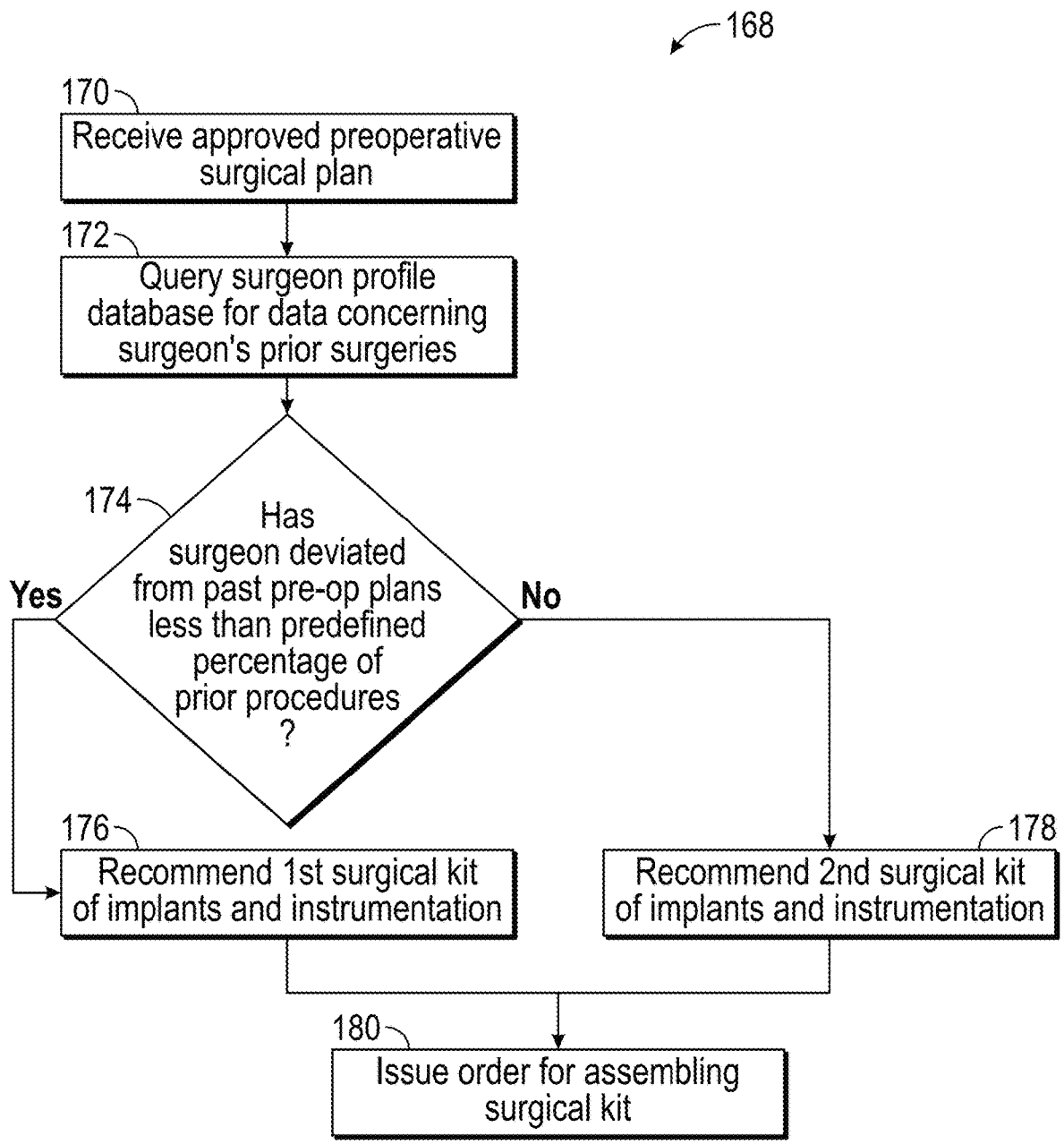
FIG. 13A schematically illustrates yet another exemplary method for planning an orthopedic procedure on a respective patient using a surgical planning system.

FIG. 13A schematically illustrates yet another method 168 for planning an orthopedic procedure for a respective patient using the system 10. The method 168 may be performed as part of a surgical planning procedure for preparing a surgical plan for the patient. Fewer or additional steps than are recited below could be performed within the scope of this disclosure, and the recited order of steps is not intended to limit this disclosure. The system 10, via any of its associated computing devices and modules, may be configured to execute each of the steps of the method 168. In an exemplary implementation, the computing device 40 of the host computer 12 may be programmed to execute the method 168. However, other implementations are further contemplated within the scope of this disclosure.

The method 168 may begin at step 170 in response to receiving a preoperative surgical plan that has been approved by a respective surgeon. The surgeon profile database 65 may then be queried at step 172 for data concerning the surgeon's prior surgeries planned using the system 10 for the procedure indicated by the approved preoperative surgical plan. The data analyzed from the surgeon profile database 65 may include the type and amount of implants actually used in the surgeon's prior surgeries, and the type and amount of implants included as part of the preoperative surgical plan for each of the surgeon's relevant prior surgeries.

At step 174, the system 10 may determine, based on a comparison of the pre-operative and post-operative data analyzed at step 172, for example, whether the surgeon has deviated from his/her past preoperative surgical plans in less than a predefined percent of his/her prior surgical procedures. In some implementations, the predefined percent may be defined as 5% of the prior surgical procedures. However, other thresholds may be established within the scope of this disclosure. In an embodiment, a "deviation" is assumed to have taken place when the surgeon changed the pre-planned procedure type, changed the pre-planned implant type, or employed a size deviation of more than one size during the prior surgical procedures.

If a YES flag is returned at step 174, a first surgical kit that includes only those implants and instrumentation necessary for executing the approved preoperative surgical may be recommended at step 176. Alternatively, if a NO flag is returned at step 174, a second surgical kit that includes a greater number of implants and instrumentation than the first surgical kit may be recommended at step 178. An order for assembling the relevant surgical kit may then be issued at step 180.

Figure 13B:
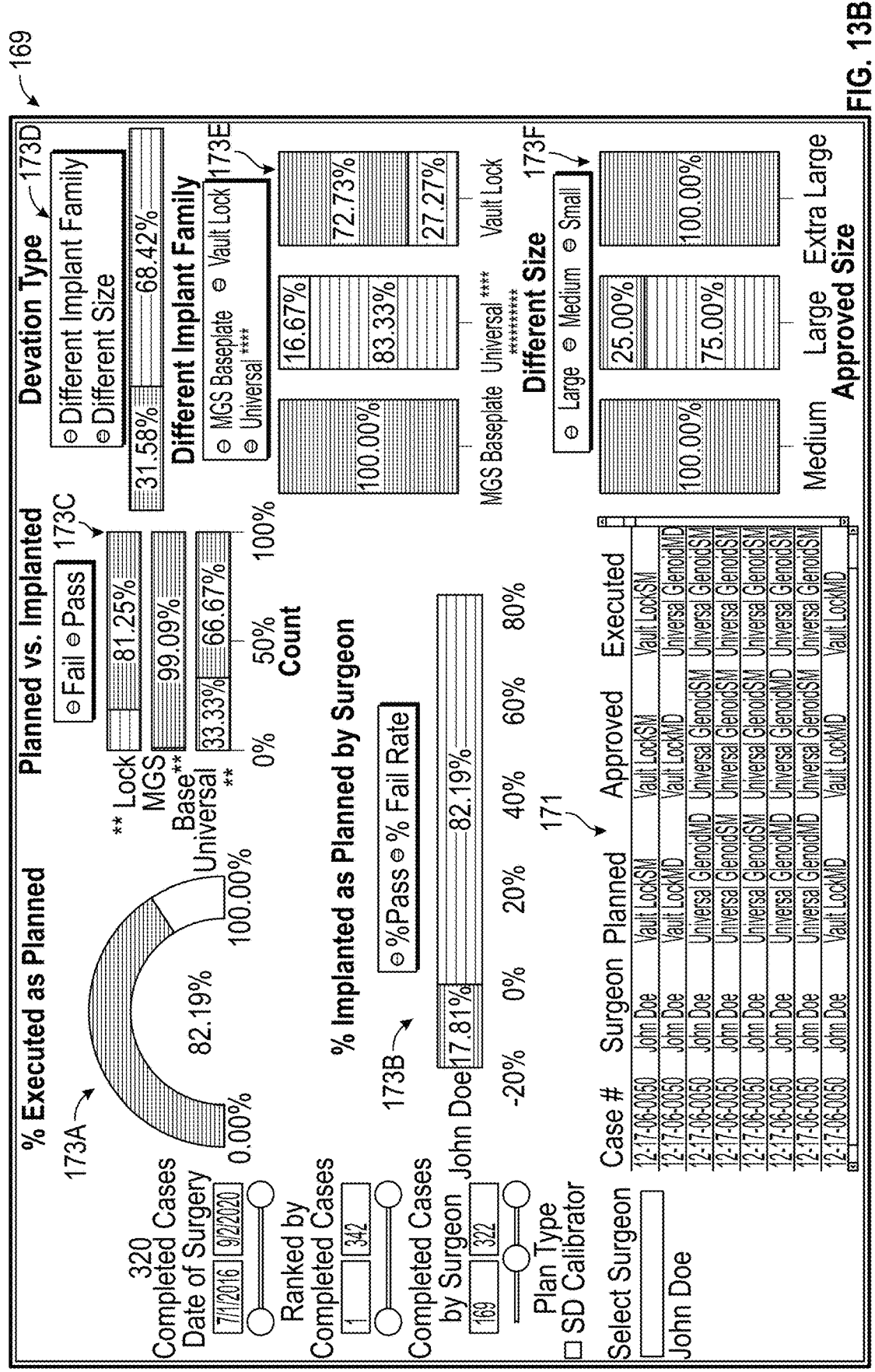
FIG. 13B illustrates yet another exemplary user interface of a surgical planning system.

FIG. 13B illustrates an exemplary deviation user interface 169 that may be provided during the method 168 discussed above. The deviation user interface 169 may be presented within the planning environment 28, for example.

The deviation user interface 169 may be configured to present various surgery-related information pertaining to a selected surgeon related to how often the surgeon has deviated from his/her past preoperative surgical plans. The deviation user interface 169 may provide a case listing 171 of the surgeon's prior surgeries and various bar graphs 173A-173F designed for conveying deviation related information to the user. For example, the bar graph 173A may illustrate the percent of prior surgeries executed as planned, the bar graph 173B may illustrate the percent of implants implanted as planned during prior surgeries, the bar graph 173C may illustrate planned versus implanted implants, the bar graph 173D may illustrate deviation type, the bar graph 173E may illustrate different implant families used in the prior surgeries, and the bar graph 173F may illustrate different sizes of implants used during prior surgeries. Other deviation related information could alternatively or additionally be conveyed to the user via the deviation user interface 169.

Figure 14:
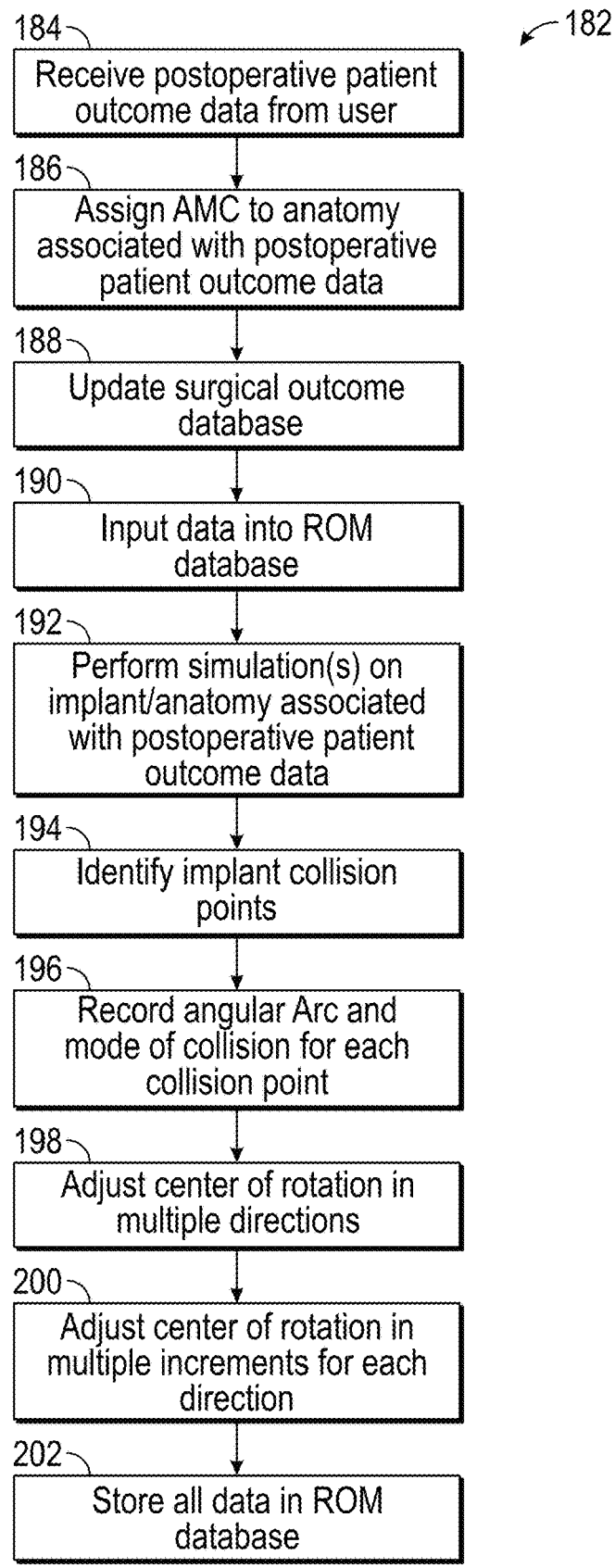
FIG. 14 schematically illustrates an exemplary method for postoperatively updating one or more databases associated with a surgical planning system.

FIG. 14 schematically illustrates a method 182 for post-operatively updating one or more databases 38 associated with the system 10. The method 182 may be performed subsequent to using the system 10 to prepare a surgical plan for a patient and subsequent to implementing the surgical plan during an actual surgery. Fewer or additional steps than are recited below could be performed within the scope of this disclosure, and the recited order of steps is not intended to limit this disclosure. The system 10, via any of its associated computing devices and modules, may be configured to execute each of the steps of the method 182. In an exemplary implementation, the computing device 40 of the host computer 12 may be programmed to execute the method 182. However, other implementations are further contemplated within the scope of this disclosure.

The system 10 may receive postoperative patient outcome data from a user at step 184. In some implementations, the postoperative patient outcome data may be manually entered by a surgeon or other staff after intraoperatively performing a surgical procedure on the patient according to a preoperative surgical plan previously created within the system 10. In other implementations, the postoperative patient outcome data may be automatically communicated to the system 10 after performing the surgical procedure as part of a closed feedback loop that can be implemented via a neural network, for example. The postoperative outcome data may include information such as the size and types of implants used during the now completed surgical procedure, the positions and orientations of the used implants, implant failure data, data related to the achievement or non-achievement of pre-operative acts of daily living goals, etc.

An anatomic makeup classification 80 may be assigned to each anatomy associated with the postoperative patient outcome data at step 186. This may be achieved, for example, by querying the anatomical makeup classification database 70 to locate bone models stored therein that have anatomical makeup classifications that are similar to the anatomical makeup classification of the anatomy indicated within the postoperative patient outcome data.

At step 188, the surgical outcomes database 66 may be updated with the information contained within the postoperative patient outcome data. For example, the surgical outcomes database 66 may be updated with the size and types of implants used during the now completed surgical procedure, the positions and orientations of the used implants, etc.

The size, type, position, and orientation of the implants indicated within the postoperative patient outcome data may be input into the range of motion database 68 at step 190. Next, at step 192, one or more motion simulations may be performed on the anatomy and implants associated with the postoperative patient outcome data. Contact or collision points may be identified at step 194 for identifying the range of motion end points for each range of motion simulation performed. The angular arc and mode of collision (e.g., implant-to-implant, implant-to-bone, bone-to-bone, etc.) for each contact point may be recorded at step 196.

The center of rotation of the implants associated with the postoperative patient outcome data may be adjusted at step 198. At step 200, the center of rotation of the implants may be adjusted relative to the respective bone model in multiple increments for recording the angular arcs and collision modes associated with the adjusted positions. All range of motion data derived from the simulations performed at steps 190-200 may then be saved within the range of motion database 68 at step 202.

The proposed surgical planning systems and methods of this disclosure may be utilized to create and implement surgical plans that are tailored to the individual patient, which may improve healing. The disclosed systems and methods may reduce complexity in implementing the surgical plans, including reduced packaging and instrumentation. In certain implementations, the system and methods may utilize feedback loops for continuously improving the recommendations provided when developing surgical plans. The proposed systems and methods therefore provide improved functionality compared to prior planning systems.

Although the different non-limiting embodiments are illustrated as having specific components or steps, the embodiments of this disclosure are not limited to those particular combinations. It is possible to use some of the components or features from any of the non-limiting embodiments in combination with features or components from any of the other non-limiting embodiments.

It should be understood that like reference numerals identify corresponding or similar elements throughout the several drawings. It should further be understood that although a particular component arrangement is disclosed and illustrated in these exemplary embodiments, other arrangements could also benefit from the teachings of this disclosure.

The foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:

1. A surgical method, comprising:
providing image data associated with an anatomy of a patient to a surgical planning system;
receiving, from the surgical planning system, an anatomical makeup classification that characterizes an anatomical makeup of a bone or a joint associated with the anatomy relative to a representative patient population,
wherein the anatomical makeup classification is a unique, multi-character identifier for describing the anatomy of the patient,
wherein each character of the unique, multi-character identifier is a unitless character;
querying a database of the surgical planning system for surgical data of other patients that have a comparable anatomical makeup classification as that assigned to the anatomy of the patient;
receiving, from the surgical planning system, a recommendation of a surgical implant that is most compatible with the anatomical makeup classification assigned to the anatomy of the patient; and
performing a surgical procedure on the patient according to the recommendation,
wherein performing the surgical procedure includes implanting the surgical implant into the bone or the joint of the patient.

2. The surgical method as recited in claim 1, wherein each character of the unique, multi-character identifier is representative of a mode that characterizes an anatomical difference in the bone or the joint across a plurality of standard deviations of anatomical variances contained within the mode.

3. The surgical method as recited in claim 2, wherein the mode is a size of the bone or the joint.

4. The surgical method as recited in claim 2, wherein the mode is a length of a subfeature of the bone or the joint.

5. The surgical method as recited in claim 2, wherein the mode is a tissue quality associated with the bone or the joint.

6. The surgical method as recited in claim 2, wherein the mode is a pre-operative range of motion of the bone or the joint.

7. The surgical method as recited in claim 1, wherein the unique, multi-character identifier is representative of a plurality of modes that characterize anatomical differences in the bone or the joint across a plurality of standard deviations of anatomical variances contained within each mode of the plurality of modes.

8. The surgical method as recited in claim 7, wherein each character of the unique, multi-character identifier represents a discrete location along a feature axis established by one of the plurality of modes and the plurality of standard deviations.

9. The surgical method as recited in claim 1, wherein the unique, multi-character identifier is at least a seven character value.

10. The surgical method as recited in claim 1, wherein the unitless character is a unitless integer.

11. The surgical method as recited in claim 1, wherein one character of the unique, multi-character identifier represents a size of the bone or the joint.

12. The surgical method as recited in claim 1, wherein one character of the unique, multi-character identifier represents a length of a subfeature of the bone or the joint.

13. The surgical method as recited in claim 1, wherein one character of the unique, multi-character identifier represents a tissue quality associated with the bone or the joint.

14. The surgical method as recited in claim 1, wherein one character of the unique, multi-character identifier represents a pre-operative range of motion of the bone or the joint.

15. The surgical method as recited in claim 1, wherein one character of the unique, multi-character identifier represents an amount of inclination of the bone or the joint.

16. The surgical method as recited in claim 1, wherein one character of the unique, multi-character identifier represents an amount of version of the bone or the joint.

17. The surgical method as recited in claim 1, wherein one character of the unique, multi-character identifier represents an amount of flexion or extension of the bone or the joint.

18. The surgical method as recited in claim 1, wherein the recommendation includes a procedure type that is most compatible with the anatomical makeup classification assigned to the anatomy of the patient.

19. The surgical method as recited in claim 1, wherein the database is a range of motion database or a surgical outcomes database.

20. A surgical method, comprising:
providing image data associated with an anatomy of a patient to a surgical planning system;
receiving, from the surgical planning system, an anatomical makeup classification that characterizes an anatomical makeup of a bone or a joint associated with the anatomy relative to a representative patient population,
wherein the anatomical makeup classification is a unique, multi-character identifier for describing the anatomy of the patient, and each character of the unique, multi-character identifier is a unitless character that is representative of a mode that describes an anatomical difference in the bone or the joint across a plurality of standard deviations of anatomical variances contained within the mode,
wherein one character of the unique, multi-character identifier represents a size of the bone or the joint, another character of the unique, multi-character identifier represents a length of a subfeature of the bone or the joint, and yet another character of the unique, multi-character identifier represents a tissue quality associated with the bone or the joint;
querying a database of the surgical planning system for surgical data of other patients that have a comparable anatomical makeup classification as that assigned to the anatomy of the patient;
receiving, from the surgical planning system, a recommendation of a surgical implant or a surgical procedure that is most compatible with the anatomical makeup classification assigned to the anatomy of the patient; and
performing a surgery on the patient according to the recommendation.

\* \* \* \* \*